(12) United States Patent
Rhoades et al.

(10) Patent No.: US 11,674,521 B2
(45) Date of Patent: Jun. 13, 2023

(54) CEILING FAN WITH GERMICIDAL CAPABILITIES

(71) Applicant: DELTA T, LLC, Lexington, KY (US)

(72) Inventors: Lennie Rhoades, Nicholasville, KY (US); Eric Evans, Lexington, KY (US); Marc McKinzie, Lexington, KY (US); Richard Lenser, Lexington, KY (US); Andrew Koukis, Danville, KY (US); Daniel Dalton, Lexington, KY (US)

(73) Assignee: DELTA T, LLC, Lexington, KY (US)

( * ) Notice: Subject to any disclaimer, the term of this patent is extended or adjusted under 35 U.S.C. 154(b) by 0 days.

(21) Appl. No.: 17/230,225

(22) Filed: Apr. 14, 2021

(65) Prior Publication Data

US 2021/0388843 A1 Dec. 16, 2021

Related U.S. Application Data

(62) Division of application No. 17/147,133, filed on Jan. 12, 2021.

(60) Provisional application No. 63/123,595, filed on Dec. 10, 2020, provisional application No. 63/054,871, filed on Jul. 22, 2020, provisional application No. 63/040,274, filed on Jun. 17, 2020, provisional application No. 63/039,788, filed on Jun. 16, 2020.

(51) Int. Cl.
*F04D 25/08* (2006.01)
*A61L 9/20* (2006.01)
*F21V 33/00* (2006.01)

(52) U.S. Cl.
CPC .............. *F04D 25/088* (2013.01); *A61L 9/20* (2013.01); *F21V 33/0096* (2013.01)

(58) Field of Classification Search
None
See application file for complete search history.

(56) References Cited

U.S. PATENT DOCUMENTS

| 4,422,824 A | 12/1983 | Eisenhardt, Jr. |
| 5,082,422 A | 1/1992 | Wang |

(Continued)

FOREIGN PATENT DOCUMENTS

| CN | 201575354 U | * | 9/2010 |
| CN | 201575354 U | | 9/2010 |

OTHER PUBLICATIONS

Fanimation (Torch Ceiling Fan—Jan. 2018—Owner's Manual V.01) (Year: 2018).*

(Continued)

*Primary Examiner* — Juan G Flores
(74) *Attorney, Agent, or Firm* — Dickinson Wright PLLC; Andrew D. Dorisio

(57) ABSTRACT

A fan for generating germicidal light is disclosed, which may be adapted to mount to a ceiling. The fan includes a hub connected to a plurality of fan blades. A motor is adapted to rotate the hub. A support is adapted to support the hub and motor from the ceiling. A lighting module may include a tray adapted to receive the support, the tray including one or more lights for providing ultraviolet germicidal light. The light may be provided by LEDs on a circuit board adapted for positioning around the support without dismounting the support from the ceiling, such as one comprised of wedge-shaped segments. The modular circuit board may form part of an uplight module supported by a housing for the motor.

27 Claims, 27 Drawing Sheets

(56) References Cited

U.S. PATENT DOCUMENTS

| | | |
|---|---|---|
| 5,151,011 A | 9/1992 | Rezek |
| 5,795,131 A * | 8/1998 | Crowhurst .............. F24F 7/007 |
| | | 416/146 R |
| 6,120,262 A | 9/2000 | McDonough et al. |
| 6,160,956 A | 12/2000 | Pelonis |
| 6,244,820 B1 | 6/2001 | Yilmaz |
| 6,461,032 B2 | 10/2002 | McKinley |
| 6,656,424 B1 | 12/2003 | Deal |
| 7,763,212 B2 | 7/2010 | McEllen |
| 7,879,299 B2 | 2/2011 | McEllen |
| 8,080,203 B2 * | 12/2011 | First .................. A61L 9/20 |
| | | 422/24 |
| 8,080,819 B2 | 12/2011 | Mueller et al. |
| 8,207,821 B2 | 6/2012 | Roberge et al. |
| 9,393,338 B2 | 7/2016 | Livchak et al. |
| 9,707,310 B2 | 7/2017 | Watanabe et al. |
| 9,901,039 B1 | 2/2018 | Dellerson et al. |
| 10,012,375 B1 * | 7/2018 | Salessi ................. F21V 7/0016 |
| 10,125,971 B2 * | 11/2018 | Graziano ............. F21V 23/003 |
| 10,207,019 B2 | 2/2019 | Takasahara et al. |
| 10,221,857 B2 | 3/2019 | Niemiec et al. |
| 10,498,099 B2 | 12/2019 | Walker et al. |
| 10,502,407 B1 | 12/2019 | Spiro |
| 10,808,964 B2 | 10/2020 | Polidoro |
| 10,897,806 B1 | 1/2021 | Bucher et al. |
| 10,987,440 B1 | 4/2021 | Sood et al. |
| 11,027,038 B1 | 6/2021 | Rhoades et al. |
| 11,060,712 B2 | 7/2021 | Niemiec et al. |
| 11,135,333 B1 | 10/2021 | Sood et al. |
| 11,236,753 B1 * | 2/2022 | Campbell ............. F04D 29/005 |
| 2005/0058584 A1 | 3/2005 | Shyu |
| 2009/0122572 A1 | 5/2009 | Page et al. |
| 2009/0129974 A1 * | 5/2009 | McEllen ............... F04D 25/088 |
| | | 422/24 |
| 2012/0126134 A1 | 5/2012 | Deal |
| 2012/0199005 A1 | 8/2012 | Koji et al. |
| 2012/0313014 A1 | 12/2012 | Stibich |
| 2013/0272879 A1 | 10/2013 | Chen |
| 2013/0291735 A1 | 11/2013 | Livchak |
| 2013/0343052 A1 | 12/2013 | Fen |
| 2015/0009666 A1 | 1/2015 | Keng et al. |
| 2015/0110625 A1 * | 4/2015 | De Siqueira Indio Da Costa ...... |
| | | F24F 7/007 |
| | | 416/5 |
| 2017/0248148 A1 | 8/2017 | Kohen |
| 2018/0055959 A1 | 3/2018 | Lin |
| 2019/0264702 A1 | 8/2019 | Huggins et al. |
| 2019/0345946 A1 | 11/2019 | Register et al. |
| 2020/0197550 A1 | 6/2020 | Barron et al. |
| 2020/0332969 A1 | 10/2020 | Soler et al. |
| 2020/0340487 A1 | 10/2020 | Register et al. |
| 2020/0366125 A1 | 11/2020 | Chen |
| 2021/0016216 A1 | 1/2021 | Popa-Simil et al. |
| 2021/0219393 A1 | 7/2021 | Kerr |
| 2021/0353813 A1 * | 11/2021 | Wald ..................... A61L 9/00 |

OTHER PUBLICATIONS

The Anatomy of a LED light Bulb—TCP Lighting (Year: 2017)*

Rhoades, et al.; USPTO Office Action dated Aug. 23, 2021 for U.S. Appl. No. 17/231,683.

Rhoades, et al.; USPTO Office Action dated Aug. 20, 2021 for U.S. Appl. No. 17/230,200.

Office Action dated Nov. 10, 2021; United States Patent and Trademark Office; Inventor: Shelly S. Wald, et al.; U.S. Appl. No. 17/319,432.

U.S. Appl. No. 63/026,702, filed May 18, 2020; Shelly S. Wald, et al.; United States Patent and Trademark Office.

U.S. Appl. No. 63/027,315, filed May 19, 2020; Shelly S. Wald, et al.; United States Patent and Trademark Office.

* cited by examiner

CEILING FAN WITH GERMICIDAL CAPABILITIES

This application is a divisional of U.S. application Ser. No. 17/147,133 filed on Jan. 12, 2021, which claims the benefit of U.S. Provisional Patent Application Ser. Nos. 63/054,871, 63/040,274, 63/039,788, and 63/123,595, the disclosures of which are incorporated herein by reference.

TECHNICAL FIELD

This document relates generally to ceiling fans and, more particularly, to a ceiling fan with germicidal capabilities.

BACKGROUND

A variety of fan systems have been made and used over the years in a variety of contexts. For instance, various ceiling fans are disclosed in U.S. Pat. No. 7,284,960, entitled "Fan Blades," issued Oct. 23, 2007; U.S. Pat. No. 6,244,821, entitled "Low Speed Cooling Fan," issued Jun. 12, 2001; U.S. Pat. No. 6,939,108, entitled "Cooling Fan with Reinforced Blade," issued Sep. 6, 2005; and U.S. Pat. No. D607,988, entitled "Ceiling Fan," issued Jan. 12, 2010. The disclosures of each of those U.S. patents are incorporated by reference herein. Additional exemplary fans are disclosed in U.S. Pat. No. 8,079,823, entitled "Fan Blades," issued Dec. 20, 2011; U.S. Pat. Pub. No. 2009/0208333, entitled "Ceiling Fan System with Brushless Motor," published Aug. 20, 2009; and U.S. Pat. Pub. No. 2010/0278637, entitled "Ceiling Fan with Variable Blade Pitch and Variable Speed Control," published Nov. 4, 2010, the disclosures of which are also incorporated by reference herein. It should be understood that teachings herein may be incorporated into any of the fans described in any of the above-referenced patents, publications, or patent applications.

A fan blade or airfoil may include one or more upper air fences and/or one or more lower air fences at any suitable position(s) along the length of the fan blade or airfoil. Merely exemplary air fences are described in U.S. Pat. Pub. No. 2011/0081246, entitled "Air Fence for Fan Blade," published Apr. 7, 2011, the disclosure of which is incorporated by reference herein. Alternatively, any other suitable type of component or feature may be positioned along the length of a fan blade or airfoil; or such components or features may simply be omitted.

The outer tip of a fan blade or airfoil may be finished by the addition of an aerodynamic tip or winglet. Merely exemplary winglets are described in U.S. Pat. No. 7,252,478, entitled "Fan Blade Modifications," issued Aug. 7, 2007, the disclosure of which is incorporated by reference herein. Additional winglets are described in U.S. Pat. No. 7,934,907, entitled "Cuffed Fan Blade Modifications," issued May 3, 2011, the disclosure of which is incorporated by reference herein. Still other exemplary winglets are described in U.S. Pat. No. D587,799, entitled "Winglet for a Fan Blade," issued Mar. 3, 2009, the disclosure of which is incorporated by reference herein. In some settings, such winglets may interrupt the outward flow of air at the tip of a fan blade, redirecting the flow to cause the air to pass over the fan blade in a perpendicular direction, and also ensuring that the entire air stream exits over the trailing edge of the fan blade and reducing tip vortex formation. In some settings, this may result in increased efficiency in operation in the region of the tip of the fan blade. In other variations, an angled extension may be added to a fan blade or airfoil, such as the angled airfoil extensions described in U.S. Pat. Pub. No. 2008/0213097, entitled "Angled Airfoil Extension for Fan Blade," published Sep. 4, 2008, and issued Apr. 24, 2012 as U.S. Pat. No. 8,162,613, the disclosure of which is incorporated by reference herein. Other suitable structures that may be associated with an outer tip of an airfoil or fan blade will be apparent to those of ordinary skill in the art. Alternatively, the outer tip of an airfoil or fan blade may be simply closed (e.g., with a cap or otherwise, etc.), or may lack any similar structure at all.

The interface of a fan blade and a fan hub may also be provided in a variety of ways. For instance, various interfaces are described in U.S. Pat. Pub. No. 2009/0081045, entitled "Aerodynamic Interface Component for Fan Blade," published Mar. 26, 2009 and issued Apr. 3, 2012 as U.S. Pat. No. 8,147,204; and U.S. Provisional Patent App. No. 61/590,469, entitled "Fan with Resilient Hub," filed Jan. 25, 2012, the disclosure of which is incorporated by reference herein. In addition, or in the alternative, the fan blade may include a retention system that couples the tip of a fan blade to an attachment point on the fan hub via a cable running through the fan blade, such as that disclosed in U.S. Pat. Pub. No. 2011/0262278, entitled "Fan Blade Retention System," published Oct. 27, 2011. Alternatively, the interface of a fan blade and a fan hub may include any other component or components, or may lack any similar structure at all.

It should also be understood that a fan may include sensors or other features that are used to control, at least in part, operation of a fan system. For instance, such fan systems are disclosed in U.S. Pat. Pub. No. 2009/0097975, entitled "Ceiling Fan with Concentric Stationary Tube and Power-Down Features," published Apr. 16, 2009, and issued Apr. 3, 2012 as U.S. Pat. No. 8,147,182, the disclosure of which is incorporated by reference herein; U.S. Pat. Pub. No. 2009/0162197, entitled "Automatic Control System and Method to Minimize Oscillation in Ceiling Fans," published Jun. 25, 2009, and issued Feb. 28, 2012 as U.S. Pat. No. 8,123,479, the disclosure of which is incorporated by reference herein; U.S. Pat. Pub. No. 2010/0291858, entitled "Automatic Control System for Ceiling Fan Based on Temperature Differentials," published Nov. 18, 2010, the disclosure of which is incorporated by reference herein; and U.S. Provisional Patent App. No. 61/165,582, entitled "Fan with Impact Avoidance System Using Infrared," filed Apr. 1, 2009, the disclosure of which is incorporated by reference herein. Alternatively, any other suitable control systems/features may be used in conjunction with embodiments described herein.

In some environments, it is desirable to sterilize the air and/or remove airborne diseases and disease vectors from the air. Existing methods for reducing airborne disease transmission between room occupants include fresh air ventilation, filtration, and direct deactivation/destruction methods such as irradiation or oxidation of the pathogens themselves. For instance, this can be achieved through the use of ultraviolet radiation (in the form of light having a particular range of short wavelengths, such as between about 200 nm and 300 nm, and is often referred to as ultraviolet germicidal irradiation (UVGI)). UVGI is a disinfection method that uses ultraviolet (UV) light at sufficiently short wavelength to kill pathogens. It is used in a variety of applications, such as food, air and water purification. UVGI utilizes short-wavelength ultraviolet radiation (UV-C) that is harmful to microorganisms. It is effective in destroying the nucleic acids in these organisms so that their DNA is disrupted by the UV radiation, leaving them unable to perform vital cellular functions. In this regard, the disclosure of U.S. Pat. No. 8,481,985 is incorporated herein by reference.

As can be appreciated, any germicidal fixture positioned in a space at a fixed location may be somewhat effective, but obviously limited in efficacy given its stationary nature (and the use of multiple stationary devices may be considered costly and inefficient in most applications) and its location away from a source of air movement, such as a fan. In many applications, such stationary devices do not receive enough airflow as a result of circulation because a typical fan is designed to force air toward the floor, and not necessarily near or toward any generator(s) of germicidal energy (which would typically be mounted on the ceiling or walls). Furthermore, many of past approaches are not implemented successfully due to lack of operator training, maintenance issues, sub-par user interfaces and experiences, cost, and are not well-adapted for retrofitting to existing fans.

Accordingly, a need is identified for an improved manner of providing a fan with a germicidal capability. In particular, the fan would be adapted to have an interchangeable lighting module in the nature of an uplight for providing sterilizing or germicidal radiation (e.g., UVGI and UC-C in particular). In some embodiments, the lighting module would be replaceable without dismounting the fan from the ceiling, and would also be adapted to provide an indication of the need for replacement and also provide certain other advantages or benefits not known in the art.

SUMMARY

According to a first aspect of the disclosure, a fan is adapted to be mounted to a ceiling and for generating germicidal light. The fan comprises a hub connected to a plurality of fan blades, a motor adapted to rotate the hub, and a support adapted to support the hub and motor from the ceiling. The fan further includes a tray adapted to receive the support, the tray including one or more lights for providing ultraviolet germicidal light (e.g., UVGI and UV-C in particular).

In one embodiment, the one or more lights are provided on a circuit board adapted to fit into the tray. The circuit board may comprise an annular structure including a plurality of interconnected substrates, each of the plurality of substrates including at least one light emitting diode for generating ultraviolet germicidal light. The tray is adapted to support the circuit board at an angle relative to a horizontal plane, and a lens may be provided for overlying the circuit board in the tray. The circuit board may be flexible, C-shaped, or formed of a plurality of semi-annular portions connected by a connector.

The circuit board may be adapted to generate visible light. The fan may also include a controller for controlling a wavelength of light produced by the one or more lights. A circuit may be for generating a signal indicative of a need to service the one or more lights based on a time of operation of the motor, such as by causing the lights to flash periodically. The fan may also optionally include a shield for shielding the one or more lights, and an optional vane for guiding air toward the one or more lights.

The tray may also include a plurality of fins for promoting heat exchange. The tray may include a stanchion adapted to engage the support. A fastener may also be provided for connecting the stanchion to the support.

According to a further aspect of the disclosure, a fan adapted to be mounted to a ceiling is provided. The fan includes a hub connected to a plurality of fan blades, a motor adapted to rotate the hub, and a support adapted to support the hub and motor from the ceiling. A modular circuit board is adapted for positioning around the support without dismounting the support (or the fan) from the ceiling.

In one embodiment, the modular circuit board includes one or more lights adapted to provide ultraviolet germicidal light toward the ceiling. The modular circuit board may comprise a plurality of semi-annular segments adapted to connect together to form an annular structure surrounding the support. A tray may be provided for supporting the modular circuit board at an angle relative to a horizontal plane.

Still a further aspect of this disclosure pertains to a fan adapted to be mounted to a ceiling. The fan includes a hub connected to a plurality of fan blades, a motor adapted to rotate the hub, and a housing for housing the motor. A support is adapted to support the hub and motor from the ceiling. An uplight module is supported by the housing for directing light at an angle relative to a horizontal plane.

In one embodiment, the uplight module comprises a tray adapted to receive the support. The tray may be adapted to support a circuit board at an angle relative to a horizontal plane. The uplight module made further include one or more lights, such as LEDs on a circuit board, for generating ultraviolet germicidal radiation. The fan may further include a circuit for generating a signal indicative of a need to service the one or more lights based on a time of operation of the motor.

Still a further aspect of the disclosure relates to a fan adapted to be mounted to a ceiling. The fan includes a hub connected to a plurality of fan blades, a motor adapted to rotate the hub, one or more lights for providing ultraviolet germicidal light, and a controller for controlling activation of the lights based on either (i) fan speed; or (ii) a motion sensor.

In one embodiment, the controller controls activation of the lights based on an indication that a fan speed is above a pre-determined amount. In other embodiments, the controller controls activation of the lights based on an indication by the motion sensor that motion is not present. The fan may also include a circuit for generating a signal indicative of a need to service the one or more lights based on a time of operation of the motor.

BRIEF DESCRIPTION OF THE DRAWING FIGURES

While the specification concludes with claims which particularly point out and distinctly claim the invention, it is believed the aspects of the disclosure will be better understood from the following description of certain examples taken in conjunction with the accompanying drawings, in which like reference numerals identify the same elements and in which:

FIG. 1 depicts a bottom perspective view of an exemplary fan;
FIG. 2 depicts a top perspective view of an exemplary fan;
FIG. 3 depicts a side view of an exemplary fan;
FIG. 4 is a top view of an exemplary fan;
FIG. 5 is a top perspective view of a support;
FIG. 6 is a bottom perspective view of a support;
FIGS. 7, 8, 9, and 10 are side views of a support;
FIG. 11 is a top view of a support;
FIG. 12 is a bottom view of a support;
FIGS. 13A and 13B are circuit diagrams;
FIG. 14 is a perspective view of a circuit board;

FIGS. 15, 16, and 17 are exploded views of an uplight module;

Figure 27:
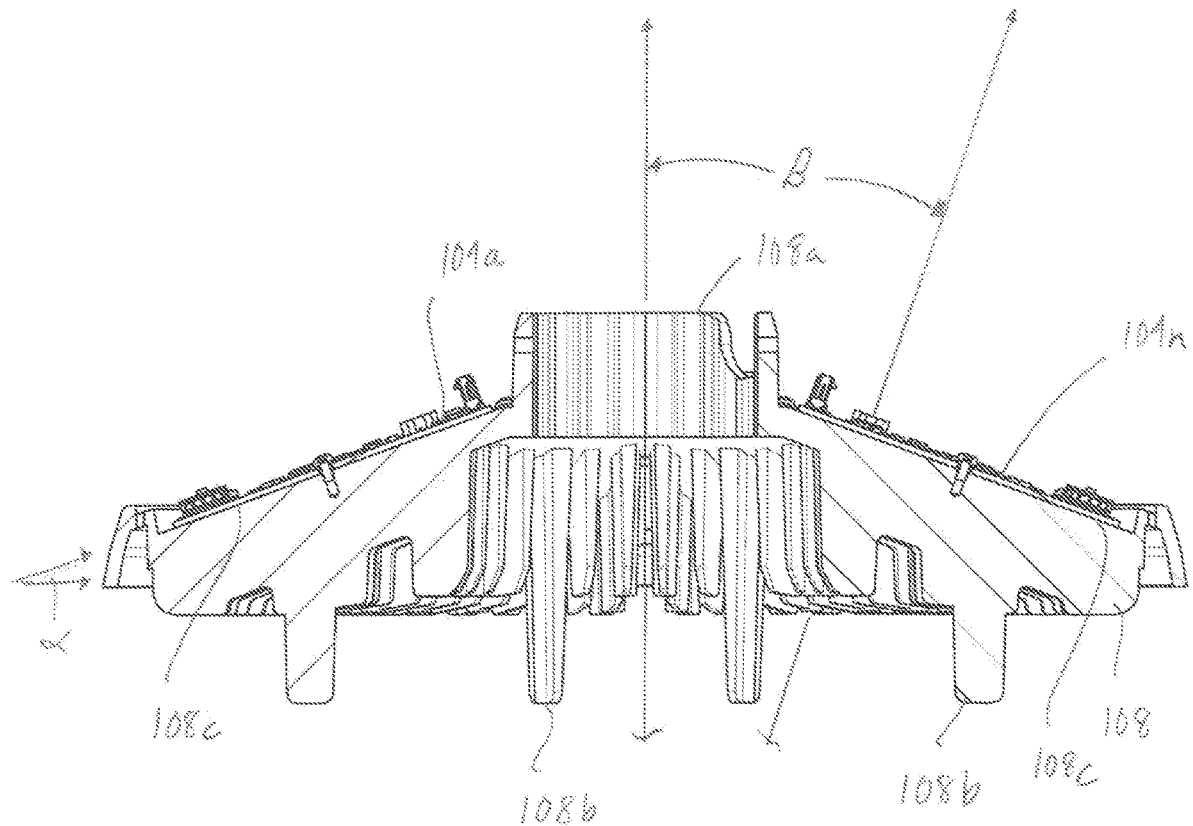
Figure 28:
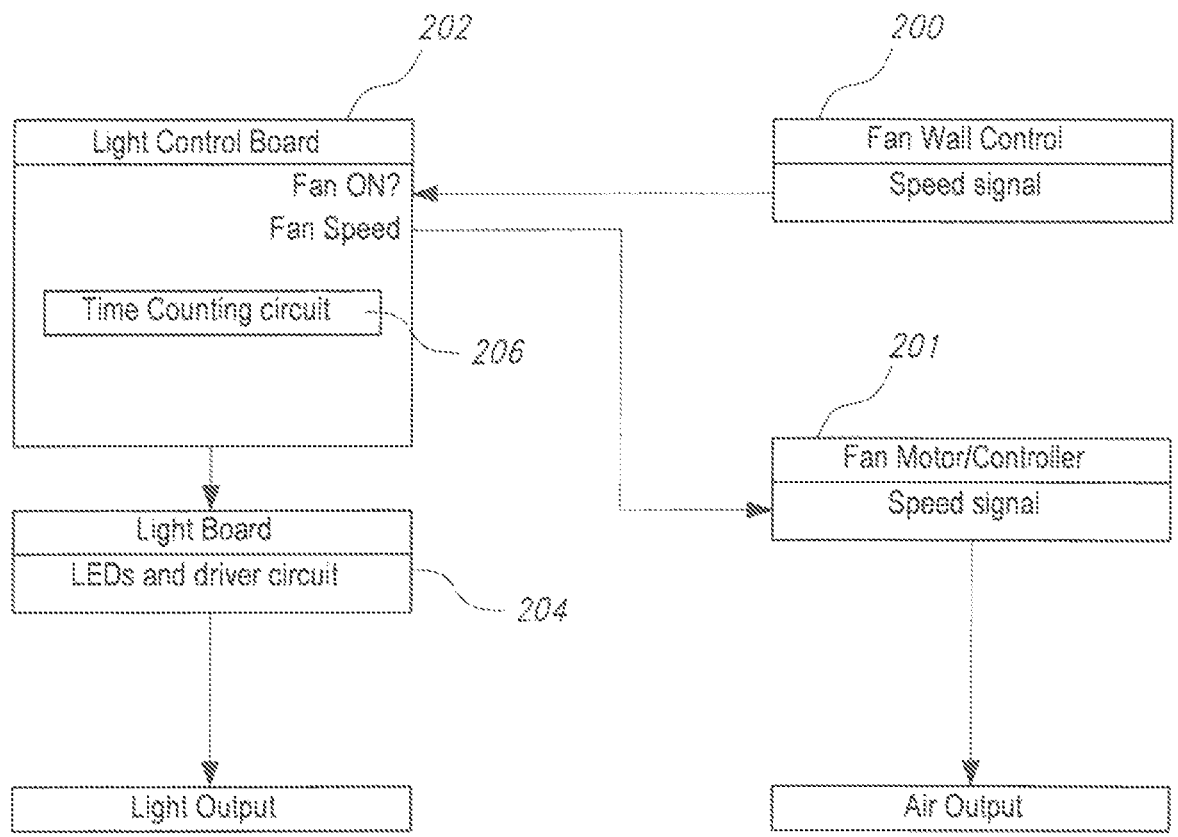
Figure 29:
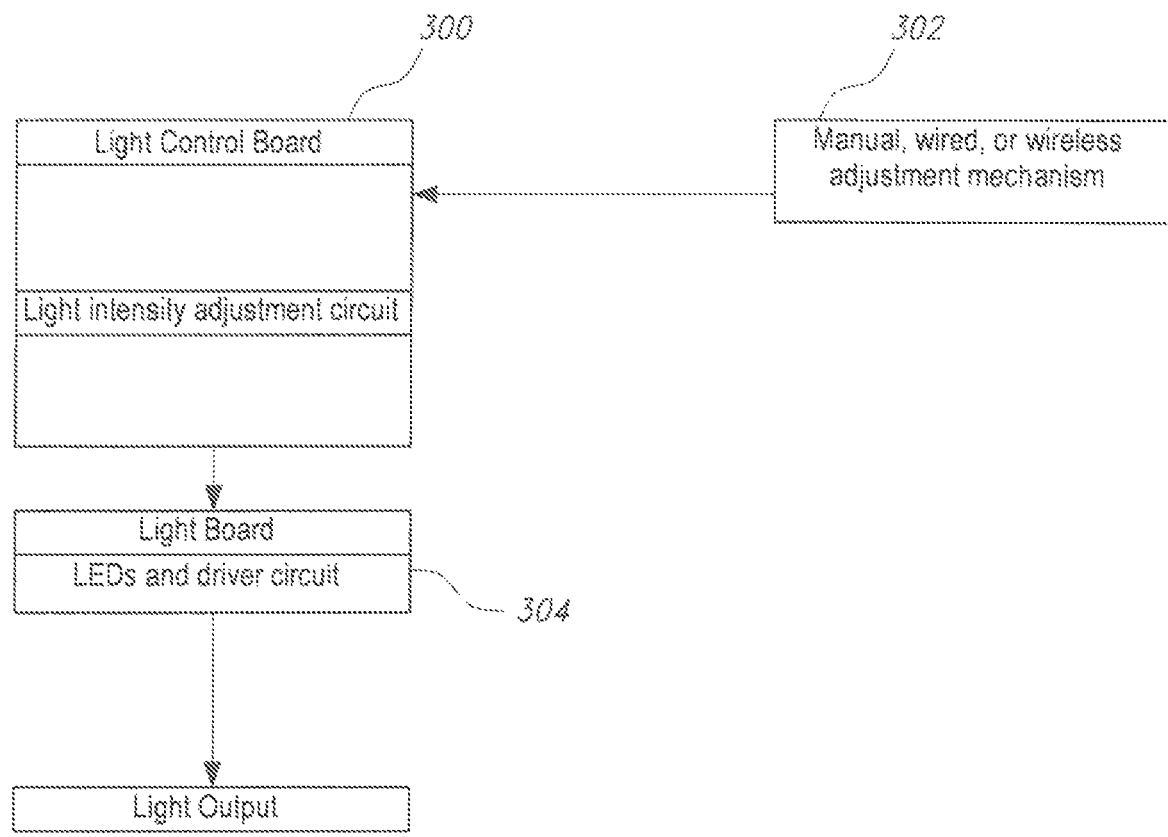

FIGS. 21, 22, 23, 24, 25, and 26 are views of another alternative version of the fan;

FIG. 27 is a cross-sectional view;

FIGS. 28 and 29 are schematic views; and

Figure 30:
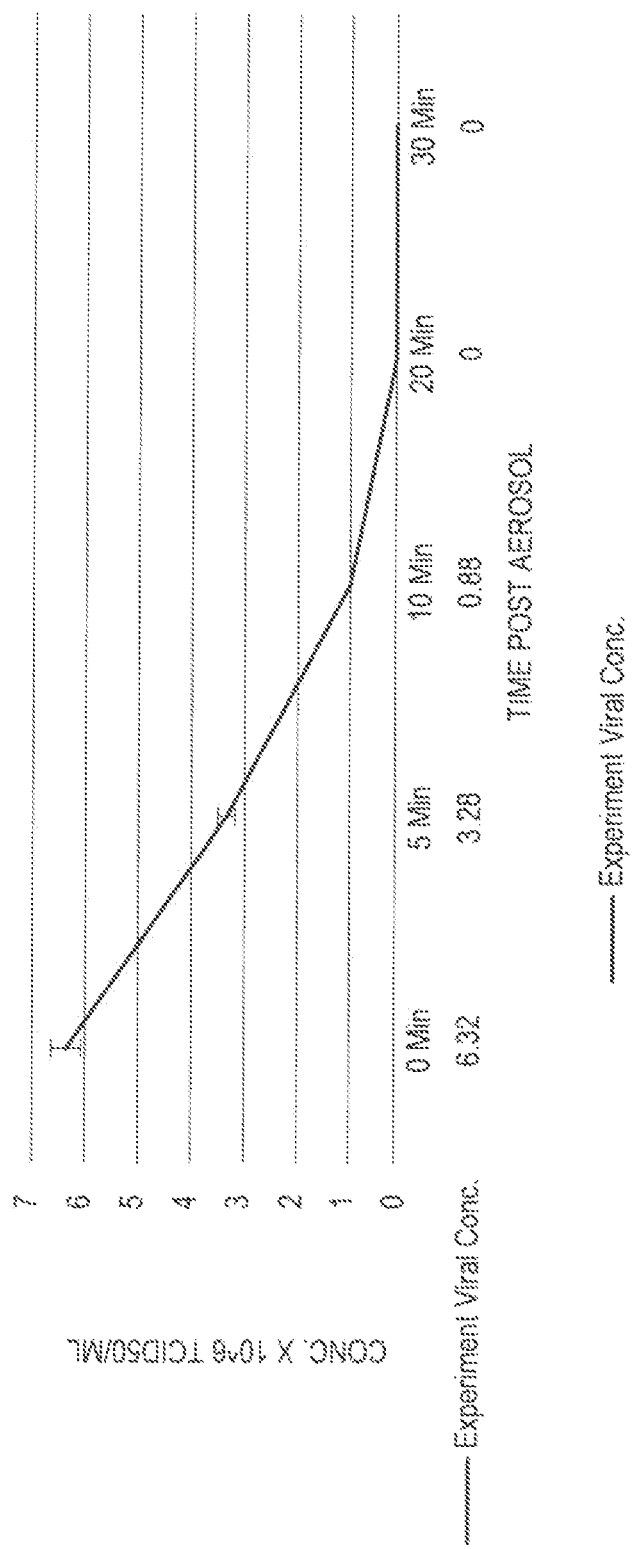

FIG. 30 is a graph illustrating the germicidal capabilities of an exemplary fan.

In the following detailed description, reference is made to the accompanying drawings that form a part hereof, and in which is shown by way of illustration, specific embodiments in which the invention may be practiced. These embodiments are described in sufficient detail to enable those skilled in the art to practice the embodiments and like numerals represent like details in the various figures. Also, it is to be understood that other embodiments may be utilized, and that process or other changes may be made without departing from the scope of the disclosure. The following detailed description is not to be taken in a limiting sense, and the scope of the invention is defined only by the appended claims and their equivalents.

DETAILED DESCRIPTION

Figure 1:
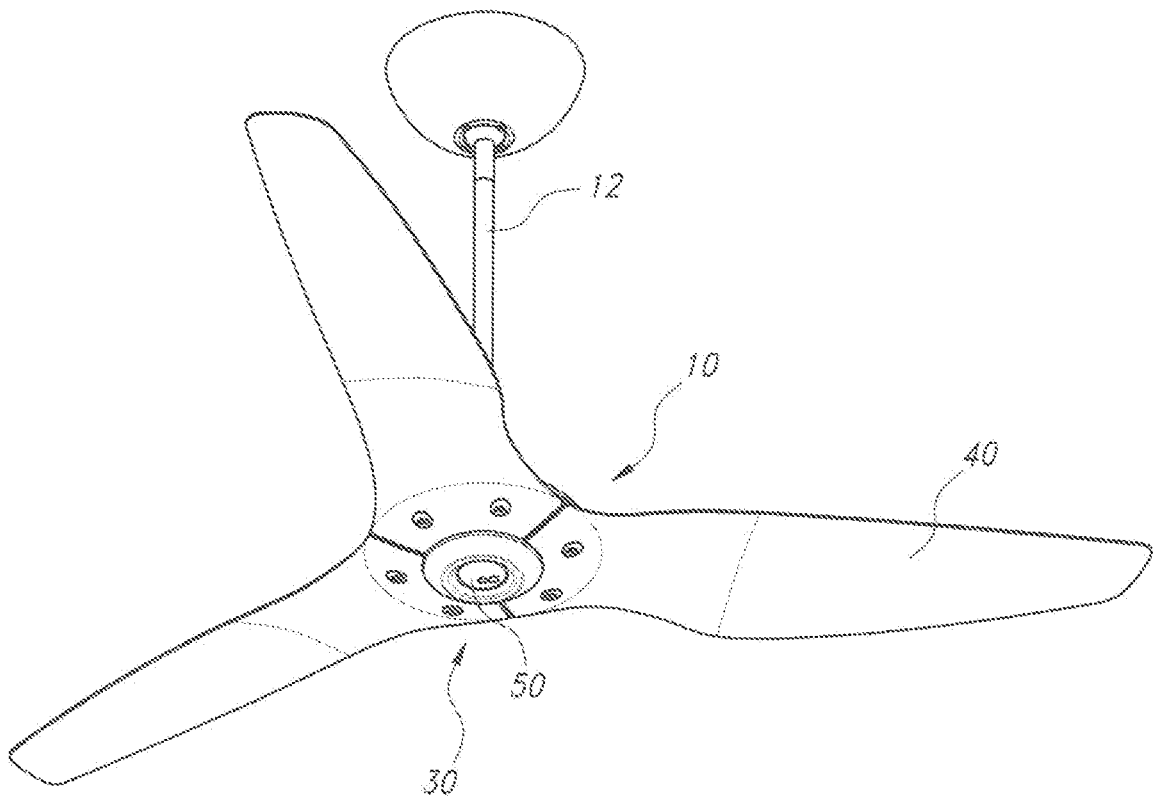

Reference is now made to FIG. 1, which depicts an exemplary fan 10 having a housing 20 containing a motor, a hub assembly 30 coupled to motor, and a plurality of fan blades 40 coupled to hub assembly 30. In the present example, fan 10 (including hub assembly 30 and fan blades 40)) has a diameter of approximately 5 feet. In some versions, fan 10 has a diameter of approximately 7 feet. In other variations, fan 10 has a diameter between approximately 6 feet, inclusive, and approximately 24 feet, inclusive. Further still, fan 10 may have any other suitable dimensions, such as 3 feet, inclusive, to 30 feet, inclusive. Except as otherwise described herein, fan 10 may be constructed and operable in accordance with at least some of the teachings of any of the references that are cited herein; and/or in any other suitable fashion. By way of example only, motor may be constructed in accordance with at least some of the teachings of U.S. Pat. Pub. No. 2009/0208333, entitled "Ceiling Fan System with Brushless Motor," published Aug. 20, 2009, the disclosure of which is incorporated by reference herein. Furthermore, fan 10 may include control electronics that are configured in accordance with at least some of the teachings of U.S. Pat. Pub. No. 2010/0278637, entitled "Ceiling Fan with Variable Blade Pitch and Variable Speed Control," published Nov. 4, 2010, the disclosure of which is incorporated by reference herein. Alternatively, motor may have any other suitable components, configurations, functionalities, and operability, as will be apparent to those of ordinary skill in the art in view of the teachings herein.

In the present example, fan 10 includes a support 12 adapted to couple the fan to a ceiling or other support structure. By way of example only, support 12 may include features of or be constructed in accordance with at least some of the teachings of U.S. Pat. Pub. No. 2009/0072108, entitled "Ceiling Fan with Angled Mounting," published Mar. 19, 2009, and issued Apr. 10, 2012 as U.S. Pat. No. 8,152,453, the disclosure of which is incorporated by reference herein, and/or in any other suitable configuration. In some versions, motor may be remote from hub assembly 30 and may be coupled via an axle or other component that is operable to transmit rotational movement from motor to hub assembly 30, which may also include an optional downlight 50, which may be concentric with the hub assembly. Still other configurations will be apparent to one of ordinary skill in the art in view of the teachings herein.

Figure 2:
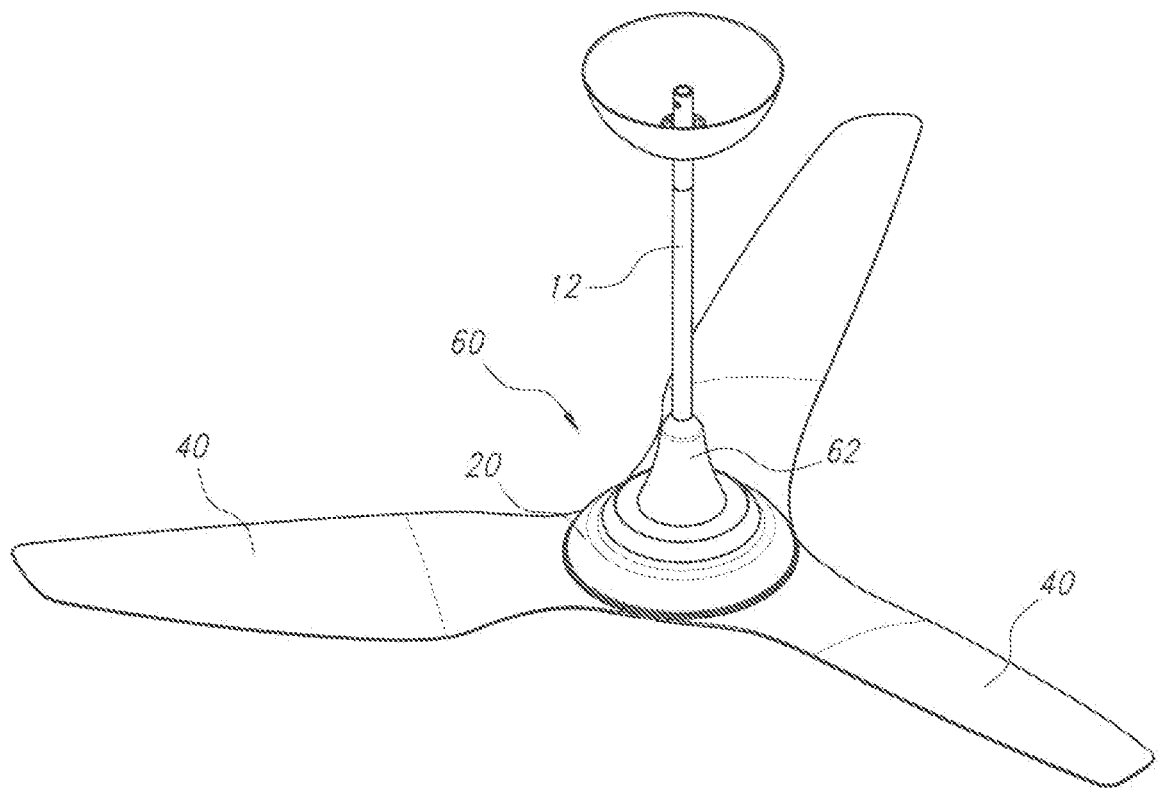
Figure 3:
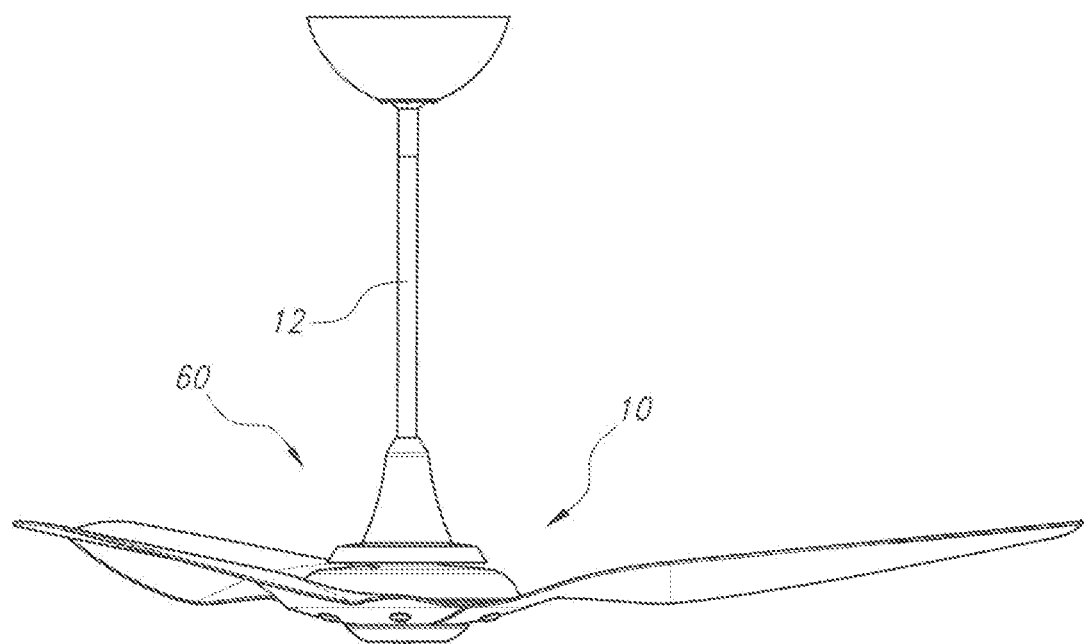
Figure 4:
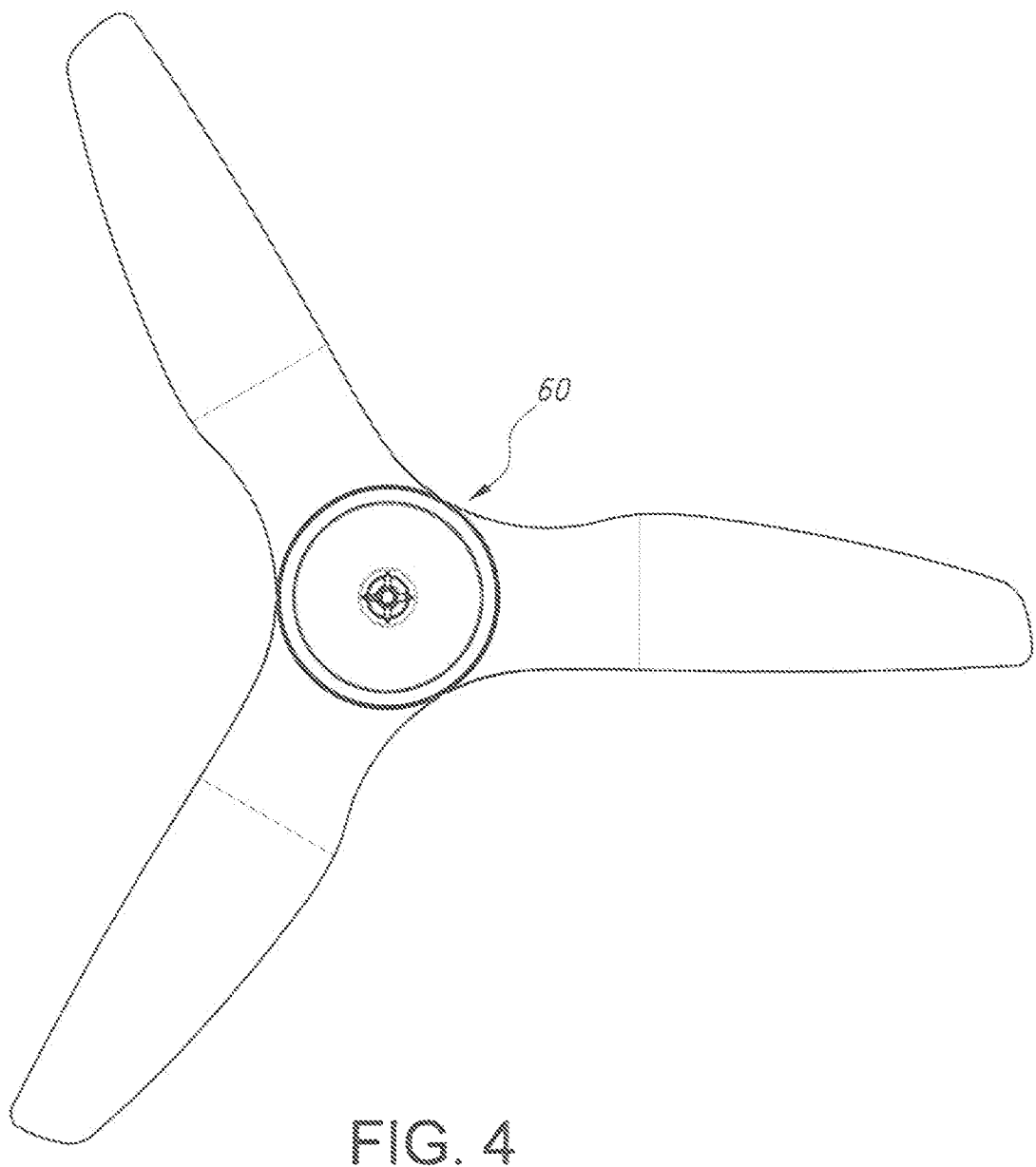
Figure 5:
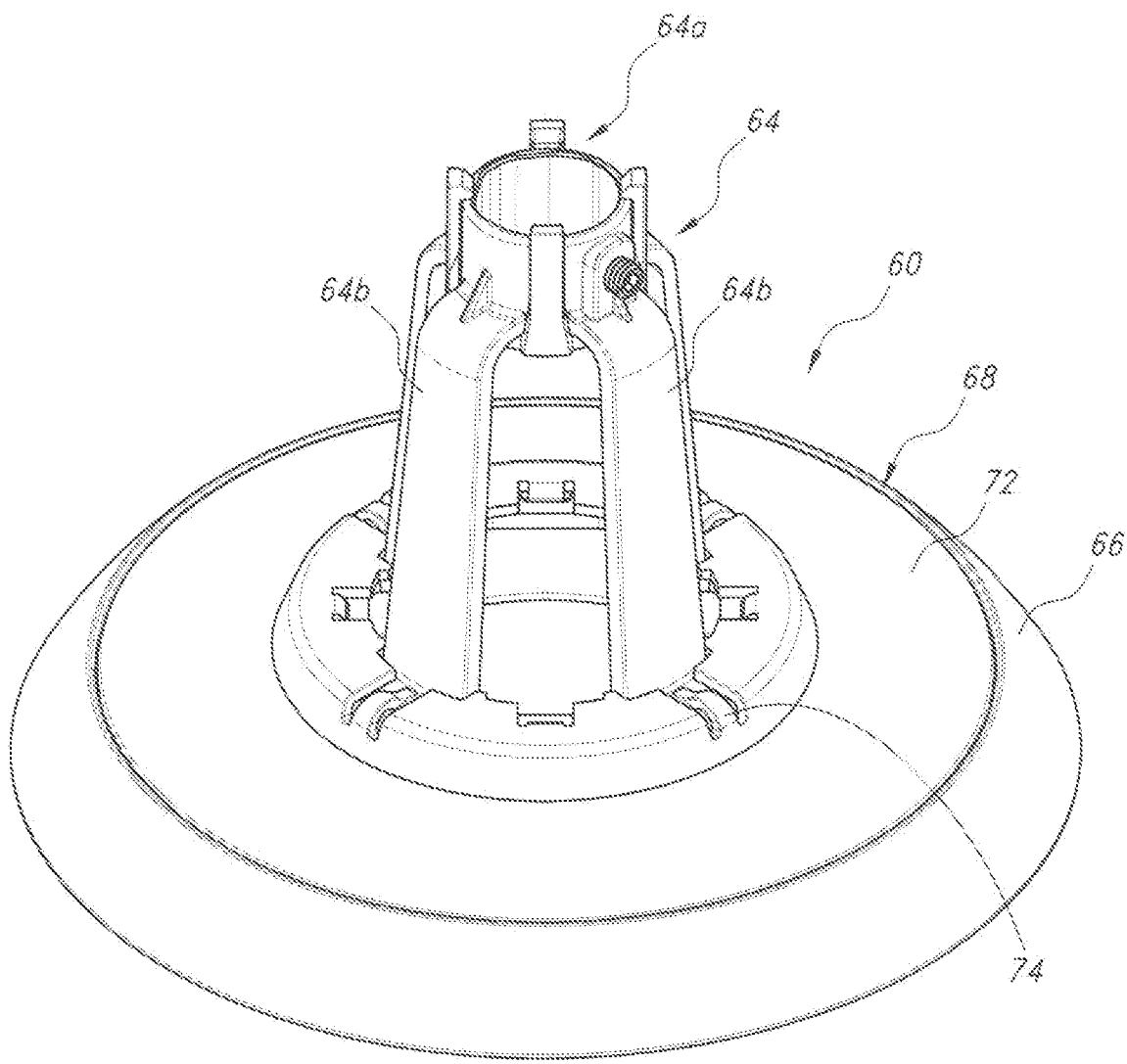
Figure 6:
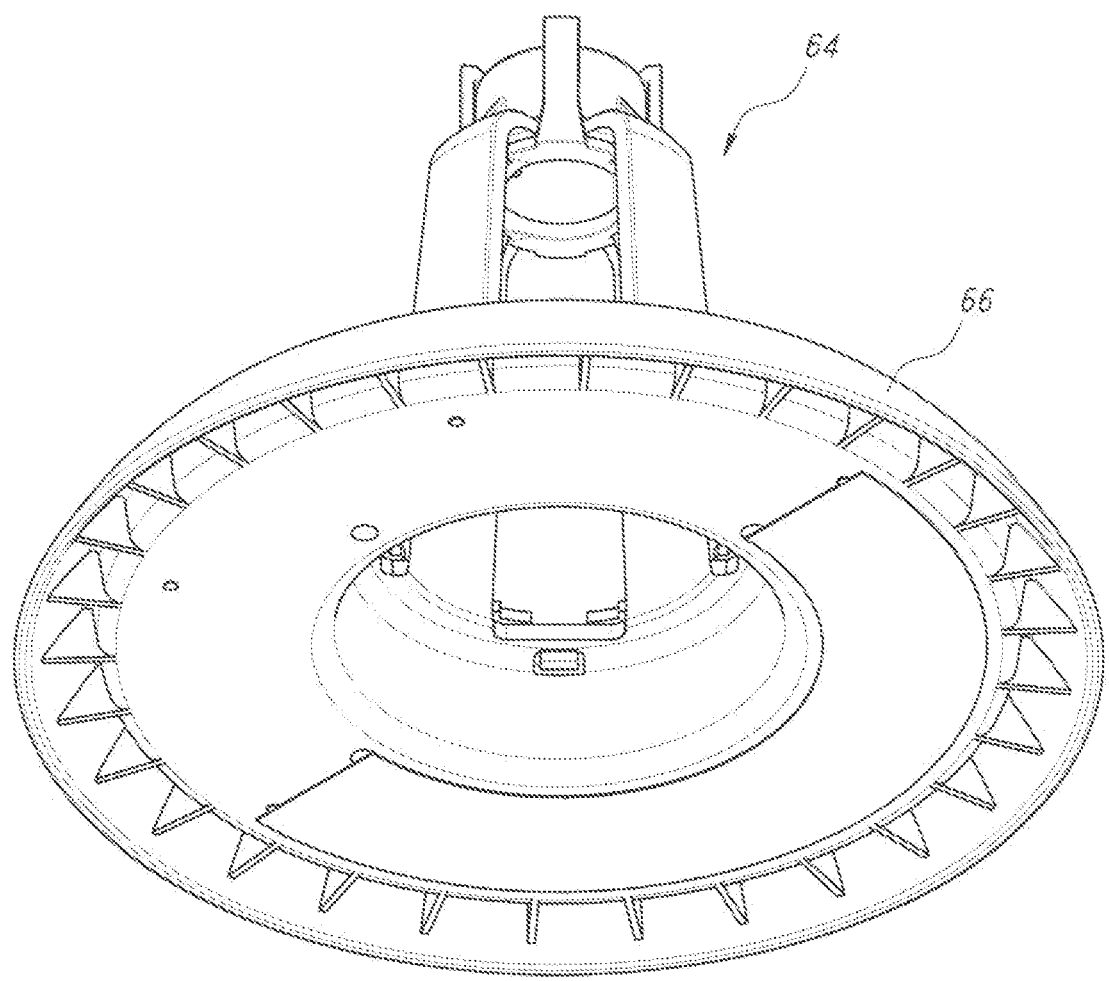
Figure 7:
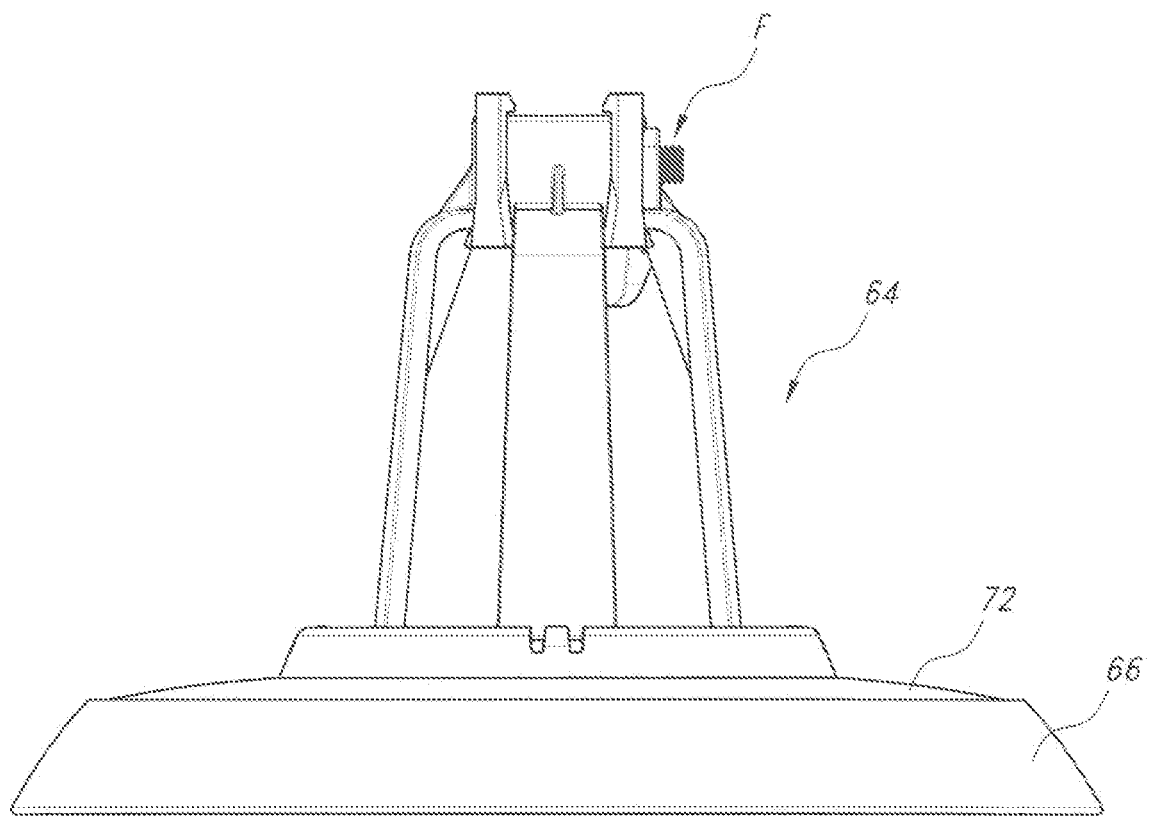
Figure 8:
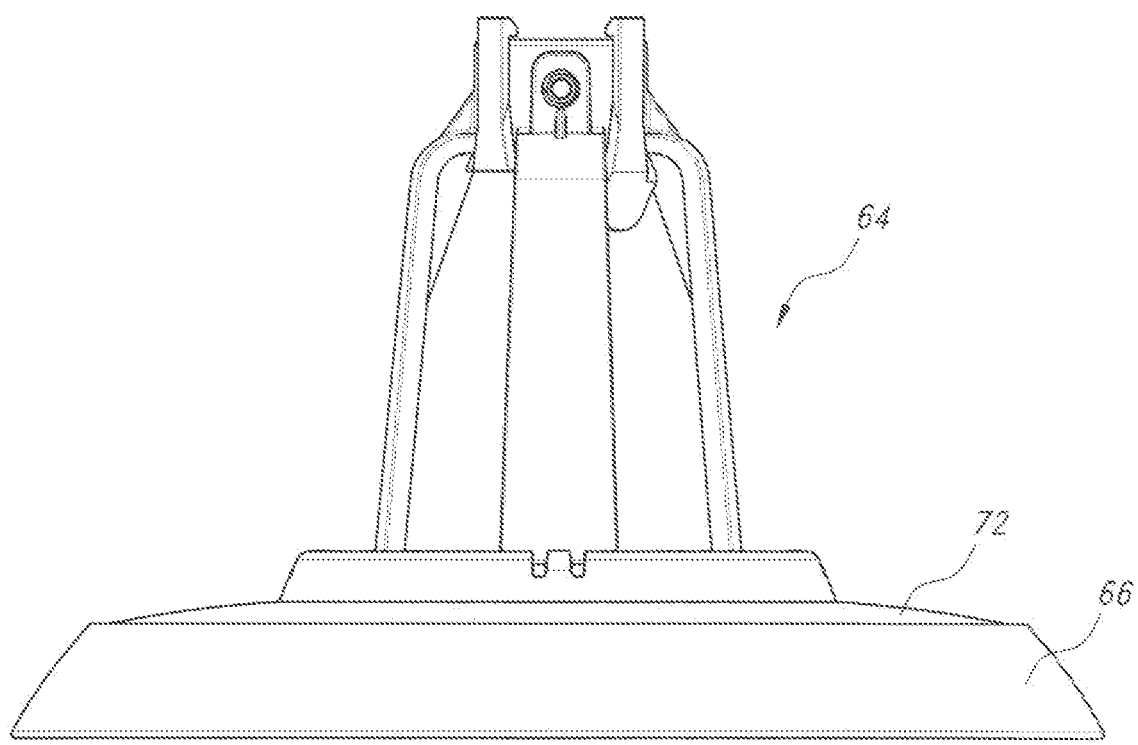
Figure 9:
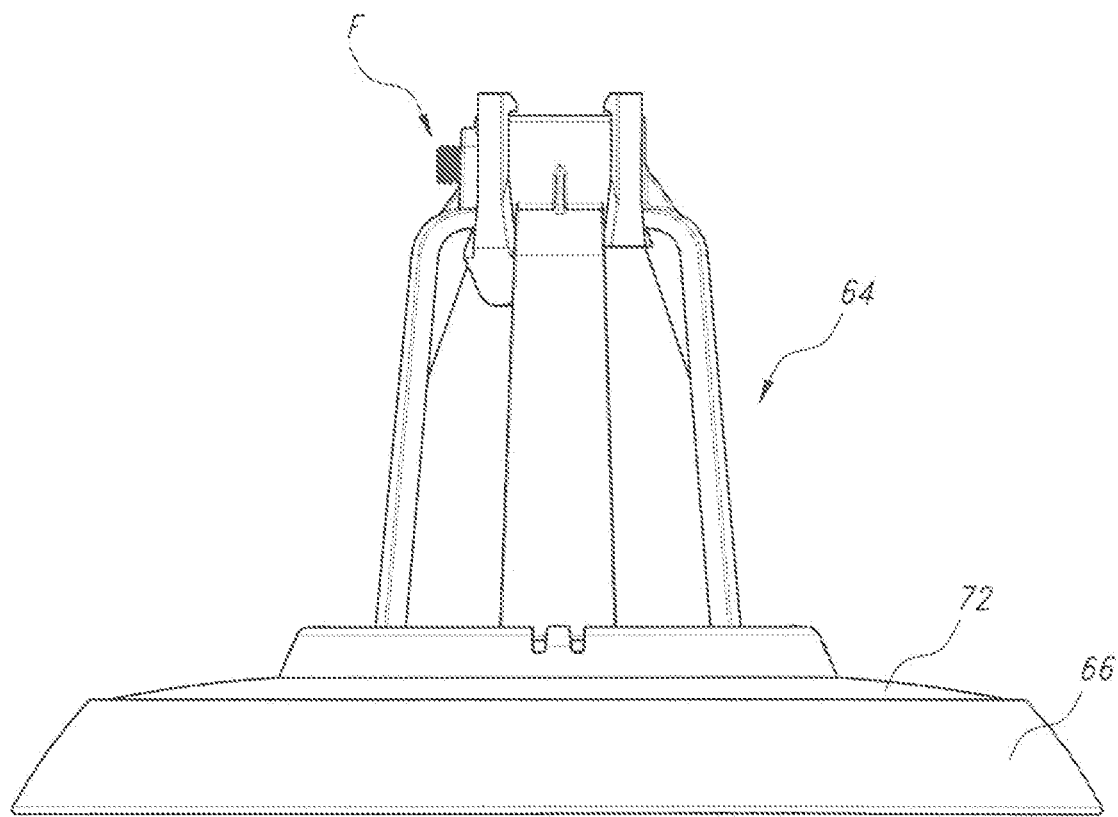
Figure 10:
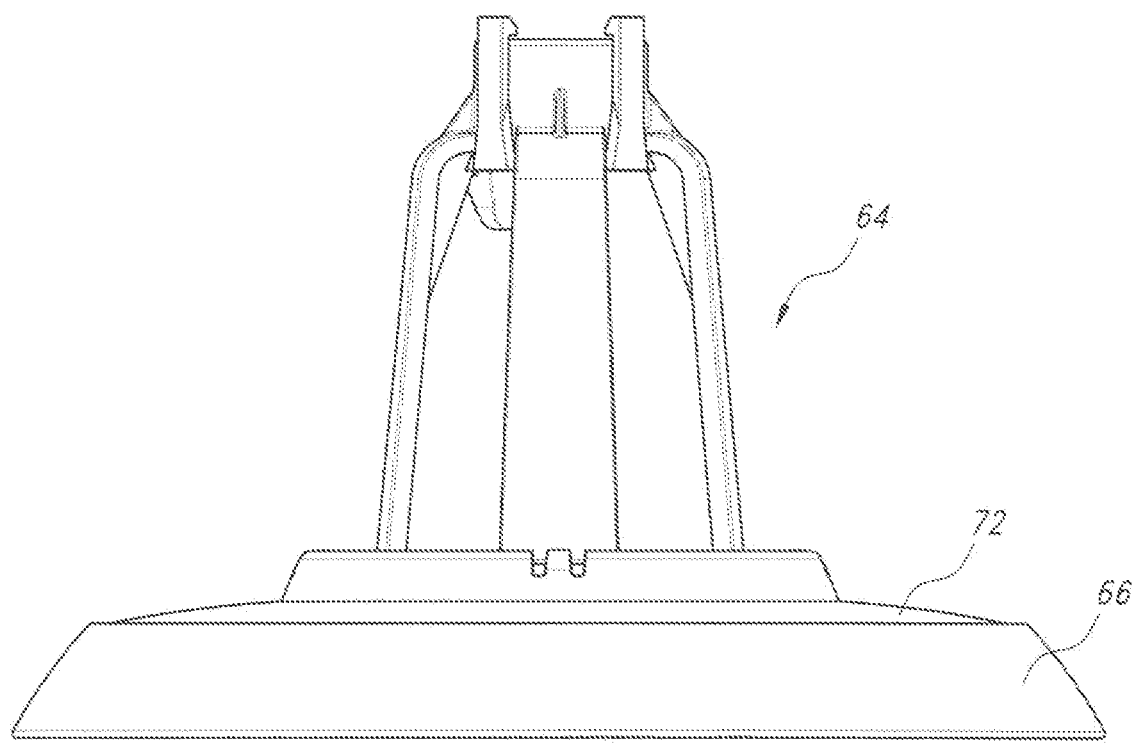
Figure 11:
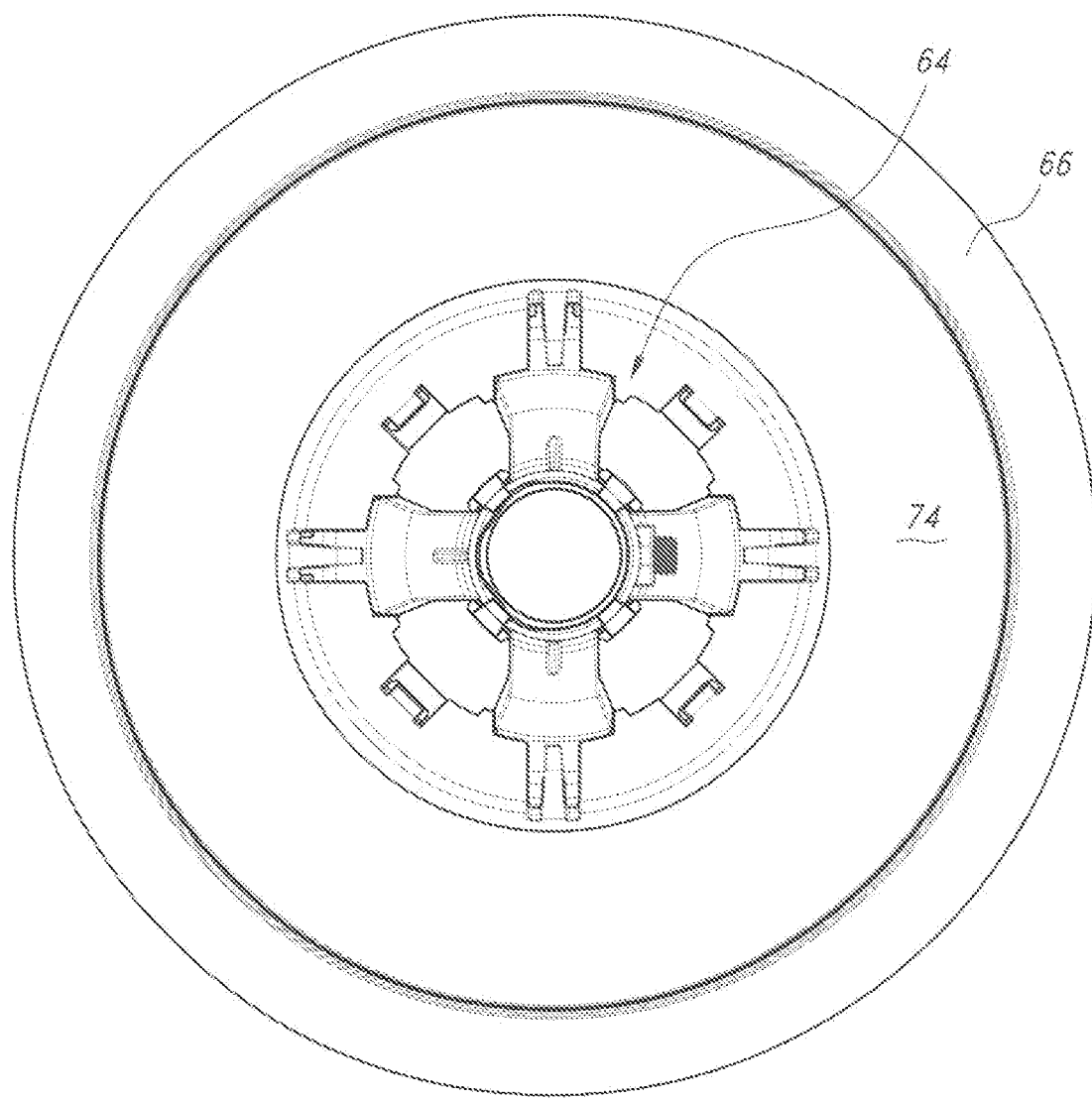
Figure 12:
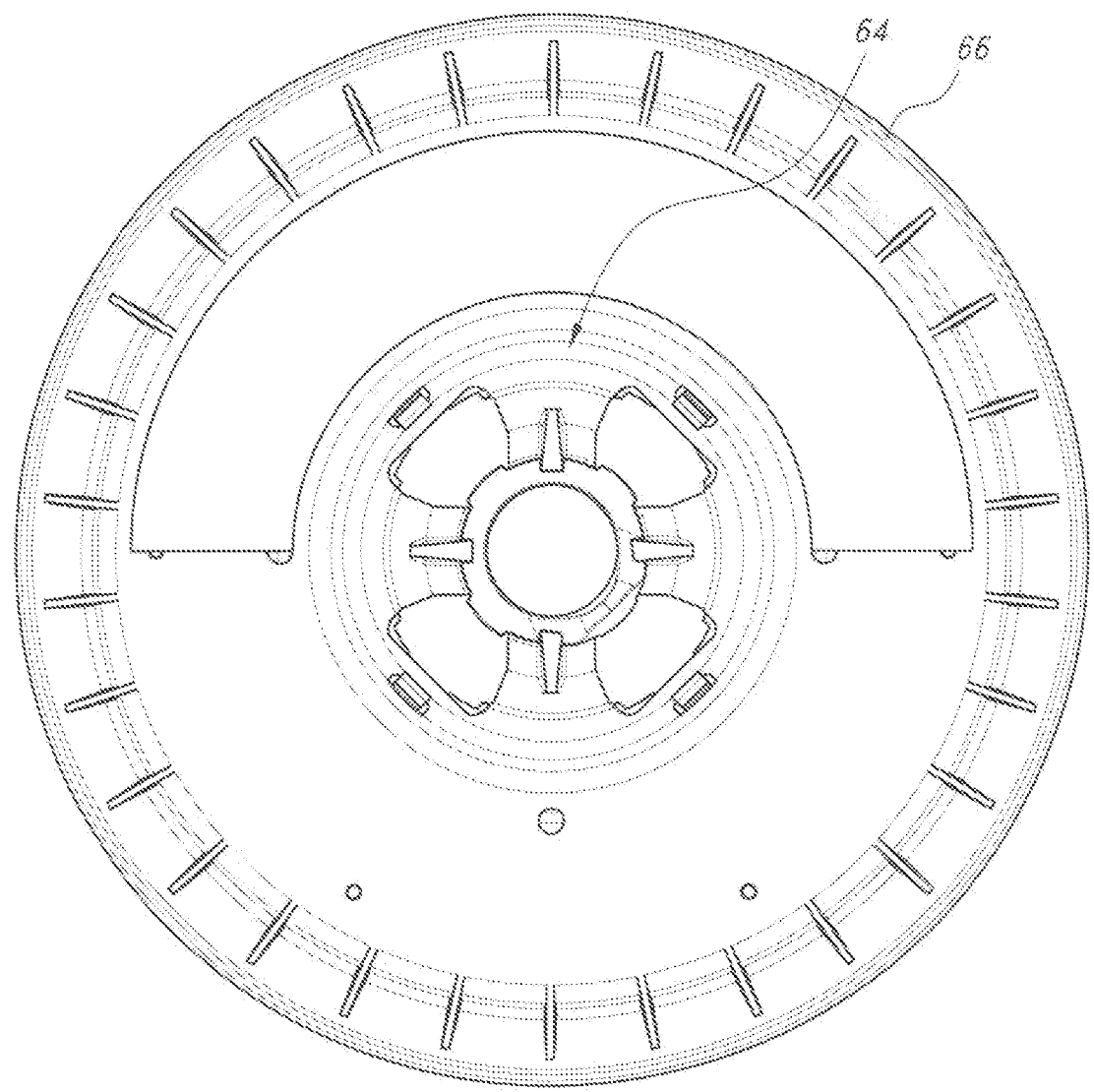
Figure 13A:
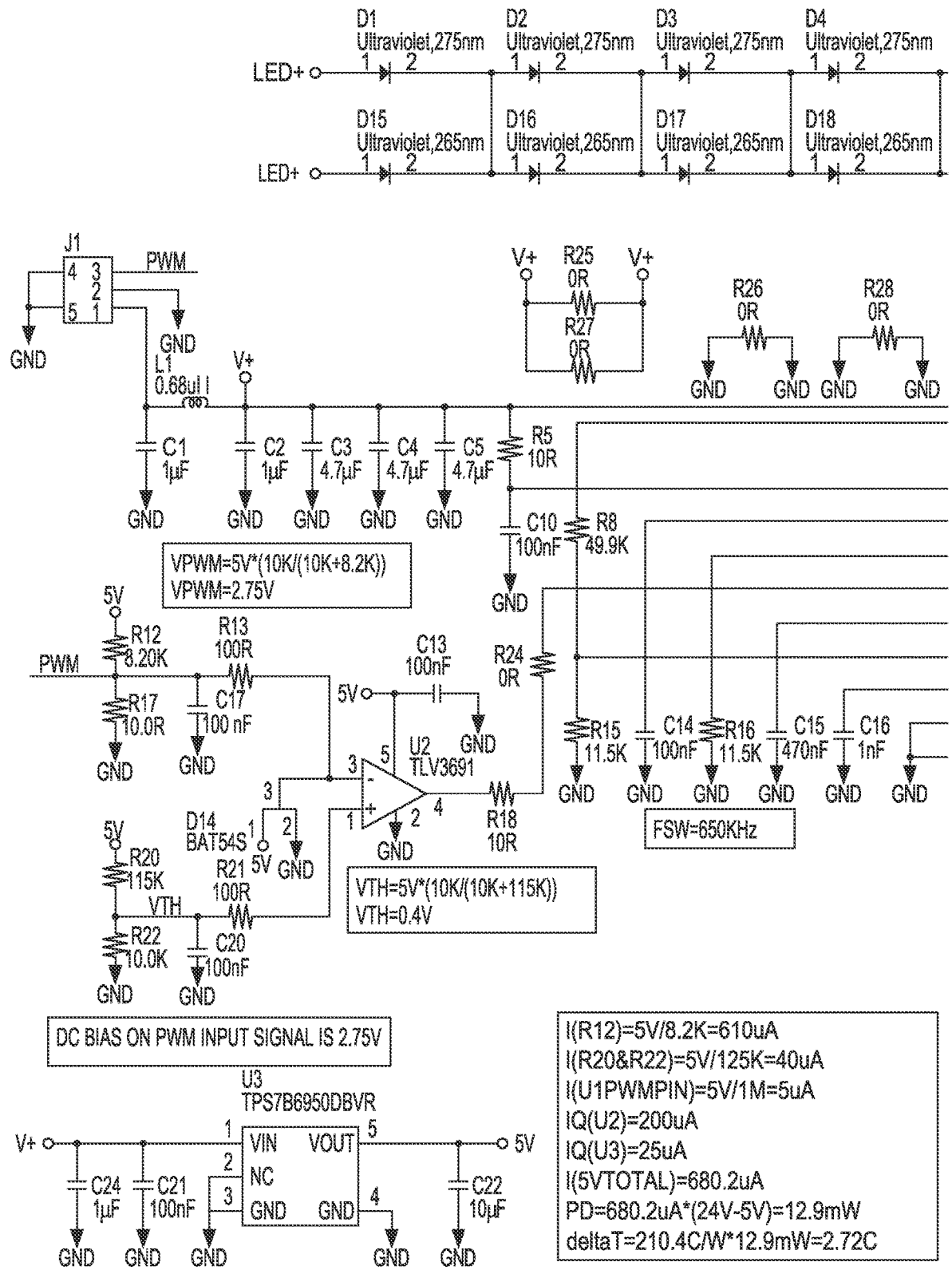
Figure 13B:
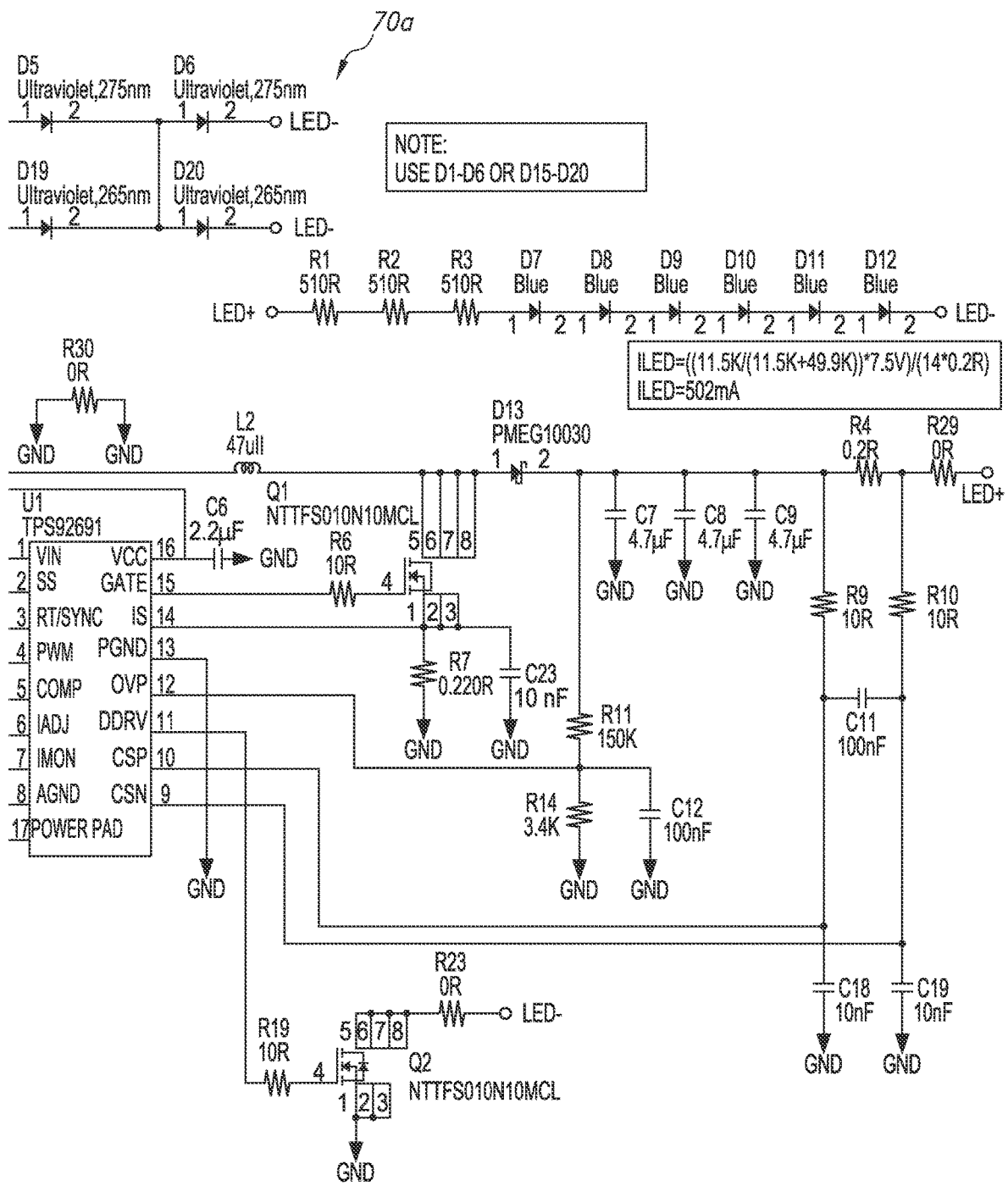

FIGS. 2-3 illustrate a manner in which the fan 10 may be provided with a lighting module 60 for providing uplight. This module 60 may be annular in nature, and adapted to overlie the motor housing 20. Specifically, the module 60 may surround the support 12, and be located between an optional frusto-conical decorative covering 62 and the motor housing 20. The module 60 may have a diameter that is less than the diameter of the housing 20, as illustrated.

With reference to FIGS. 4-13, a specific example of the lighting module 60 is described. An upwardly projecting portion of the module 60 may comprise a stanchion 64 having an annular opening 64a for receiving the support 12, and depending supports 64b for underlying the covering 62. The stanchion 64 may be connected to an annular base 66 forming a recess in the nature of an annular tray 68 having a peripheral lip and a recessed portion (see also FIG. 16) for receiving one or more lights on an upper support surface thereof, such as for example LED(s) for emitting light of a selected wavelength, either for providing general lighting, providing germicidal capability, or both depending on a selected mode of operation. The stanchion 64 may also be provided with a fastener F for connecting it with the support 12 (see FIGS. 7 and 9).

Figure 14:
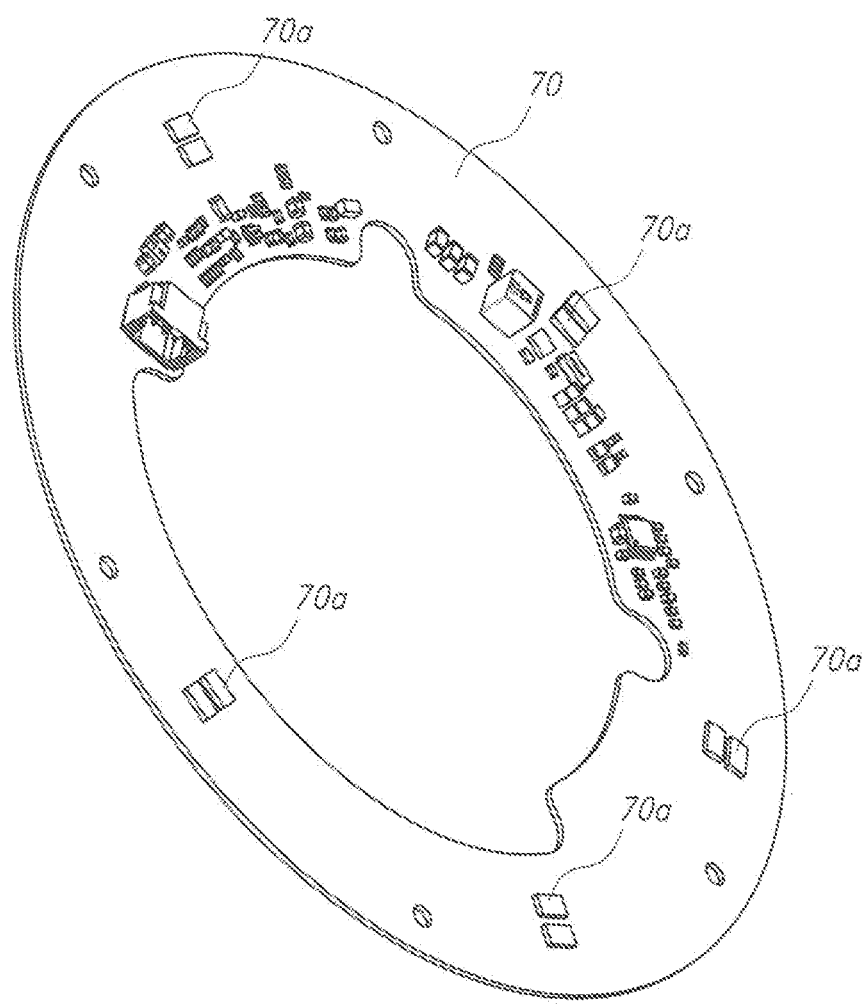

In the illustrated embodiment, the LED(s) for providing uplight are arranged on a circuit board (which may be an insulated board on which conductive pathways are constructed and components are mounted), such as a printed circuit board assembly 70 (PCBA, see FIG. 14). The PCBA 70 may be annular in nature, but not necessarily circular. The PCBA 70 may be adapted to connect to a power supply, such as that associated with the fan 10, as indicated in the circuit diagram of FIGS. 13A and 13B. The connection may be by way of a releasable plug or connector to promote interchangeability, as outlined further in the following description.

Overlying the tray 68 and the PCBA 70 when present is an optional lens 72. The lens 72 may comprise an annular transparent or translucent material that overlies the PCBA 70 and allows light to pass therefrom in a direction opposite the base 66, which may be opaque. The lens 72 may include one or more releasable connectors 74 for connecting with the base 66, such as along a radially inward portion for engaging corresponding portions of the stanchion 64. These connectors 74 allow for the lens 72 to be disconnected and then raised or lowered relative to the base 66, such as long the support 12 with which it is generally concentric.

The module 60 may be positioned over the support 12 of the fan 10 prior to installation, or even in a retrofit situation by removing the fan 10 from the ceiling temporarily and positioning the module thereupon. When connected to the power supply, the lighting provided by LEDs 70a associated with the PCBA 70 thus provides the fan 10 with uplight capability (that is, light directed upwardly toward the ceiling to which the fan is mounted), which may be turned on or off as the user desires (such as by way of a remote control). In the case where the LEDs 70a provide UVGI, the uplighting provided thus gives the fan 10 germicidal capabilities (which may be indicated by providing the LEDs with a particular color of light, such as for example blue, to indicate to the remote user that the germicidal capabilities are enabled).

As can be appreciated, the lighting capabilities may be made interchangeable by simply changing out the PCBA 70. Specifically, if it is desired for a fan 10 to provide general lighting, a PCBA 70 with "regular" or visible wavelength LEDs may be used. If germicidal capability is desired, a PCBA 70 with LEDs providing UVGI light may be provided instead, such as by simply removing the lens 72 if present and exchanging the PCBAs. Thus, the disclosure may be considered to propose a kit comprising the fan 10 or module 60 with two different forms of uplighting (e.g., PCBAs with different types of LEDs, such as one for providing "regular" uplighting and one for providing UVGI uplighting). As indicated in the circuit diagram in FIGS. 13A and 13B, the LEDs 70a may produce light having two different wavelengths in the lower UV band, such as 265 nm and 275 nm (six of each in this example, but any desired number could be used). A single PCBA could also have LEDs for producing both UVGI and regular light, and a remote control could be used to toggle between the two versions.

Figure 15:
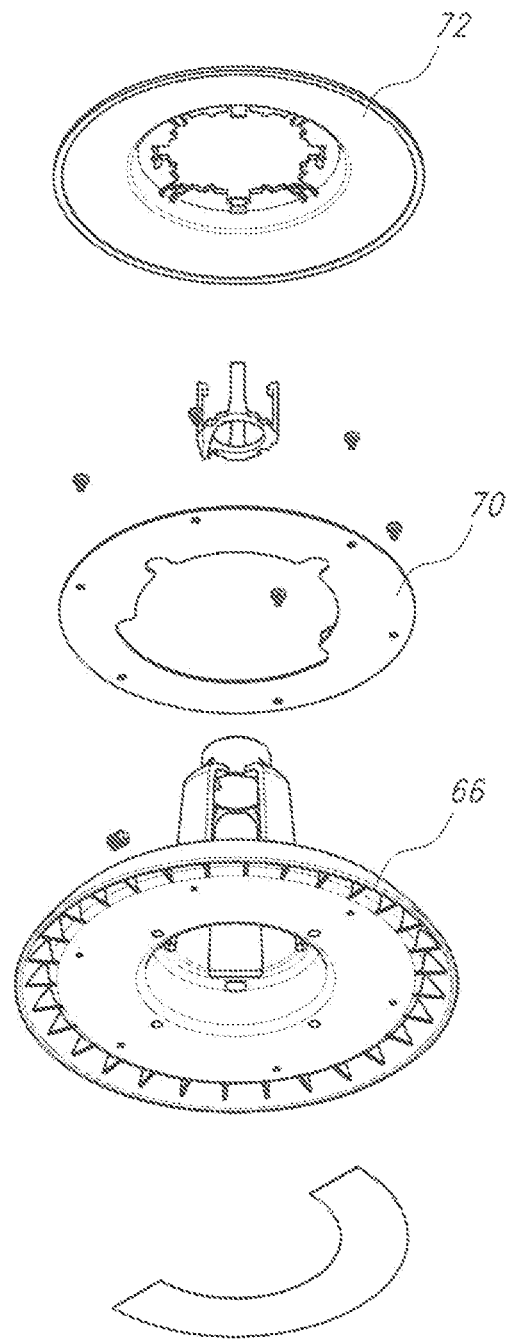
Figure 16:
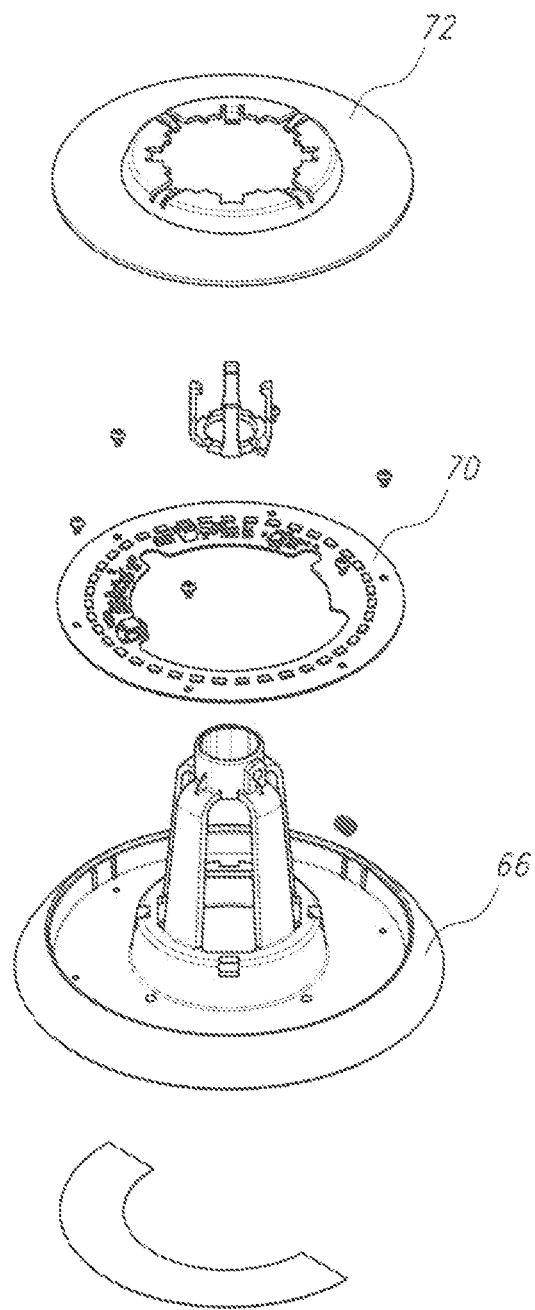

To facilitate exchange, and with reference to the exploded view of FIGS. 15-16, it can be understood that the PCBA 70 may simply be removed from the base 66 by disassembling the module 60 and replaced, as desired. Specifically, the lens 72 if present may be simply disconnected and raised along the support (not shown), and the PCBA 70 installed in the tray 68. The lens 72, if present, may then be replaced and connected with module 60. As can be appreciated, this allows for the end user to easily replace the PCBA 70 in case the LED(s) fail, or if it is desired to substitute regular lighting for UVGI, or vice-versa.

Figure 17:
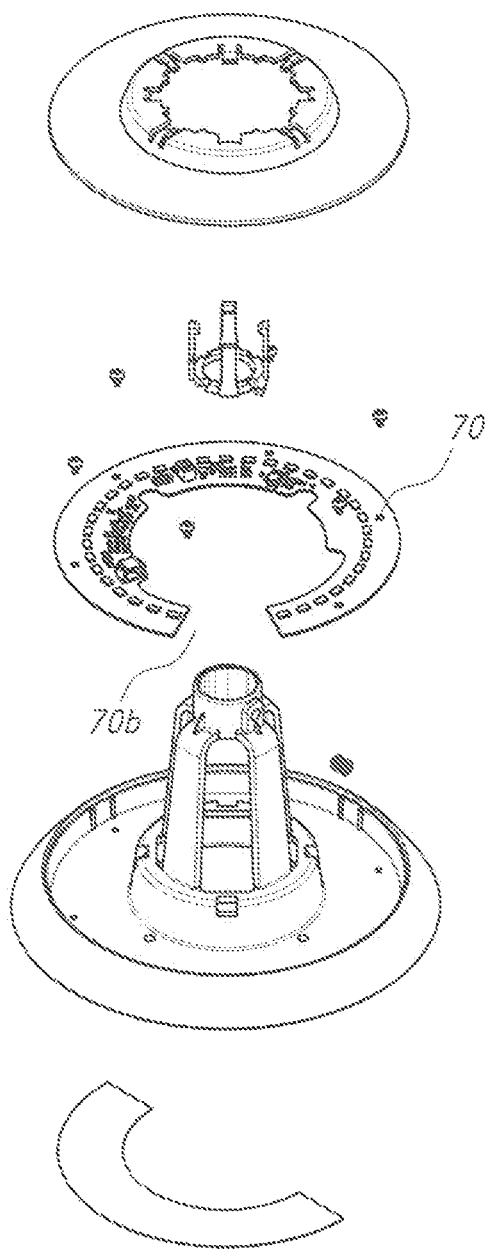

In an alternative version, as shown in FIG. 17, the PCBA 70 may be provided with a notch or cutout 70b sized and shaped to receive the support 12. Using this type of arrangement allows for the PCBA 70 to be installed or exchanged on a ceiling-mounted fan 10 without the need to dismount the same. In other words, the support 12 and the fan 10 may remain connected to the ceiling, while the PCBA 70 is disconnected, removed, and replaced, either with an identical replacement or a different version for providing uplight of a different type.

A single PCBA could also have LEDs for producing both UVGI and regular light. A remote control (including possibly a handheld computer or mobile phone) could be used to toggle between the two, such as by including one or more buttons. Such a remote control could also have an indicator, such as a light, to indicate when the UV is activated. In another example, a motion sensor (such as for example, an infrared detector) may also be used to turn the LEDs on and off (including in the "on" condition when motion is not detected, such as for a pre-determined amount of time). Likewise, the on/off condition of the LEDs may be controlled based on fan speed (e.g., the LEDs are automatically turned on when the fan motor is operational, or the speed is above a certain pre-determined threshold to ensure that germicidal capability is maximized).

Figure 18:
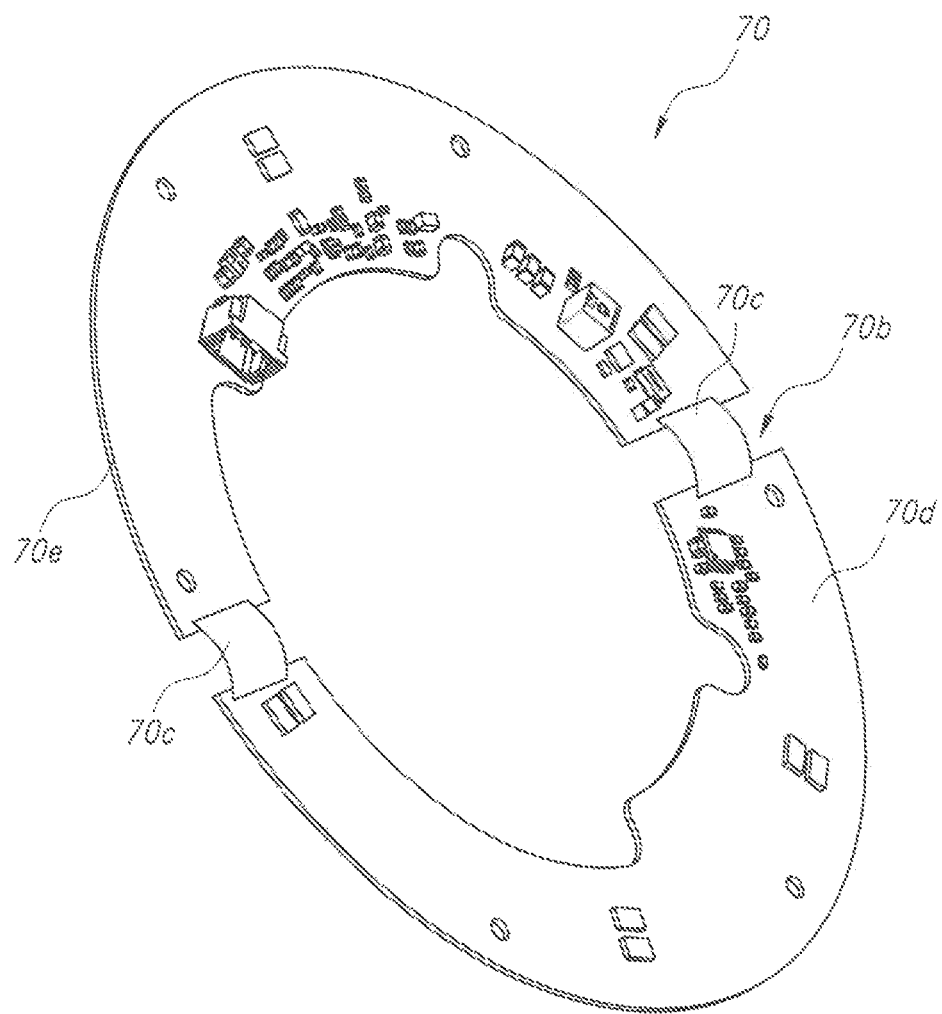
FIG. 18 is a perspective view of a modular circuit board.

Turning to FIG. 18, the PCBA 70 could also be made flexible. This may be achieved by having a notch 70b and a flexible connector 70c connecting portions 70d, 70e. The flexible connector 70c may comprise a substrate of a flexible material (e.g., Kapton) and internal or embedded electrical conductors, such as copper wires, for interconnecting the segments. One or more of the portions 70d, 70e may include one or more light generators, such as an LED for generating UVGI. The portions may comprise a plurality of semi-annular structures (that is, having a shape resembling part of a ring or incomplete circular band), and thus form an annular ring when connected, but may take other shapes as well. In this way, the two or more portions may be flexed relative to each other for removal from over the support without the need to dismount the fan from the ceiling.

Figure 19:
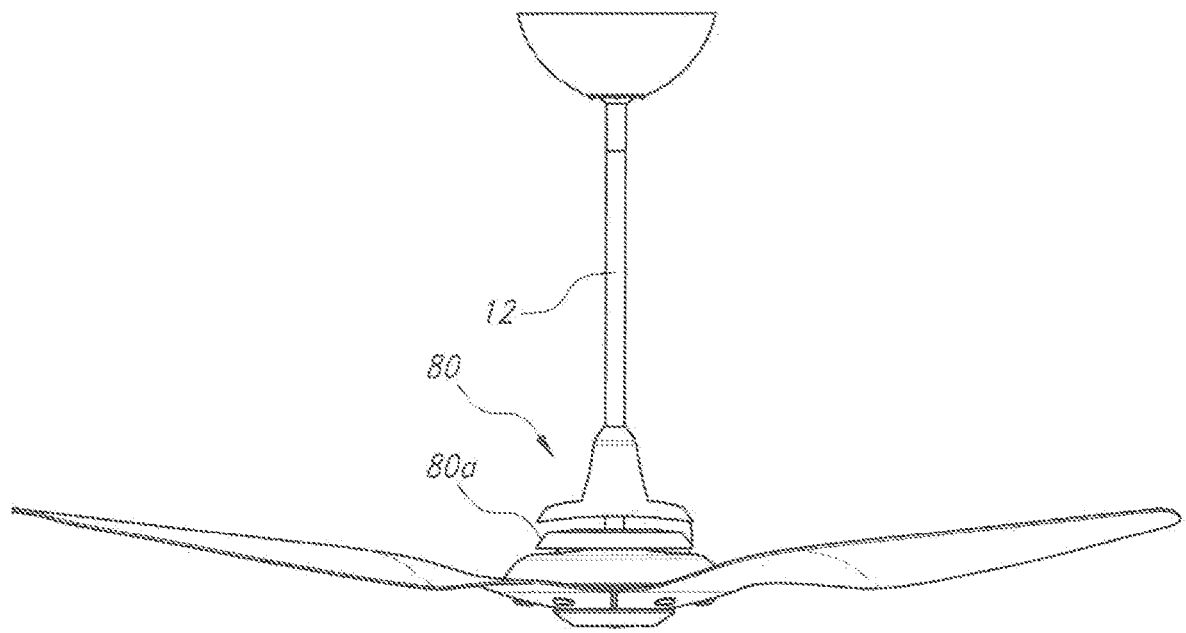
FIG. 19 is a side view of an alternative version of the fan.
Figure 20:
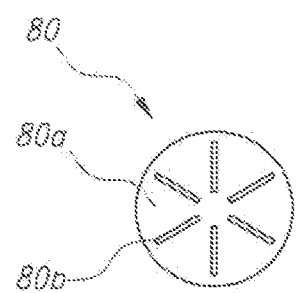
FIG. 20 is a top view of a light shield.
Figure 21:
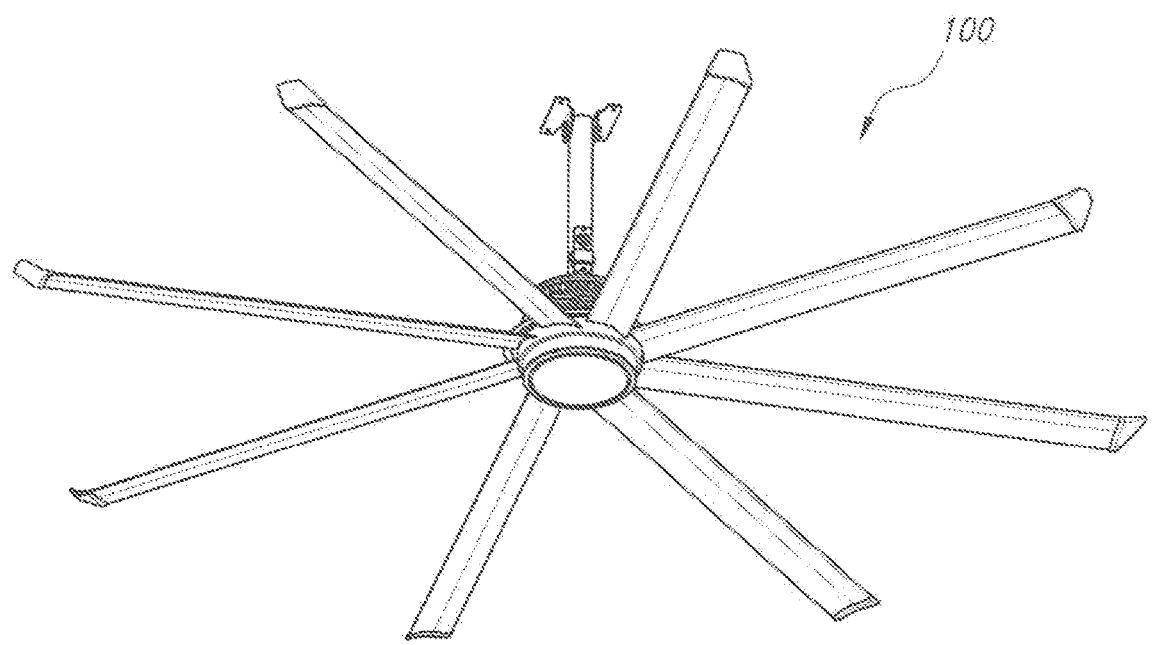
Figure 22:
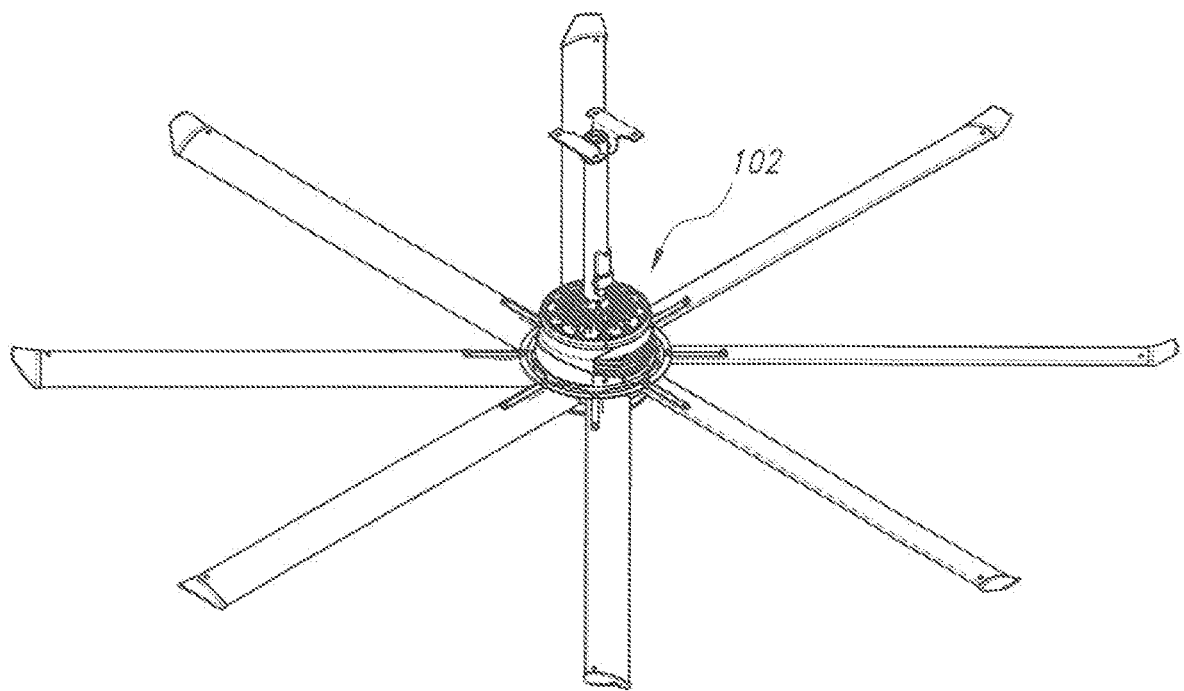
Figure 23:
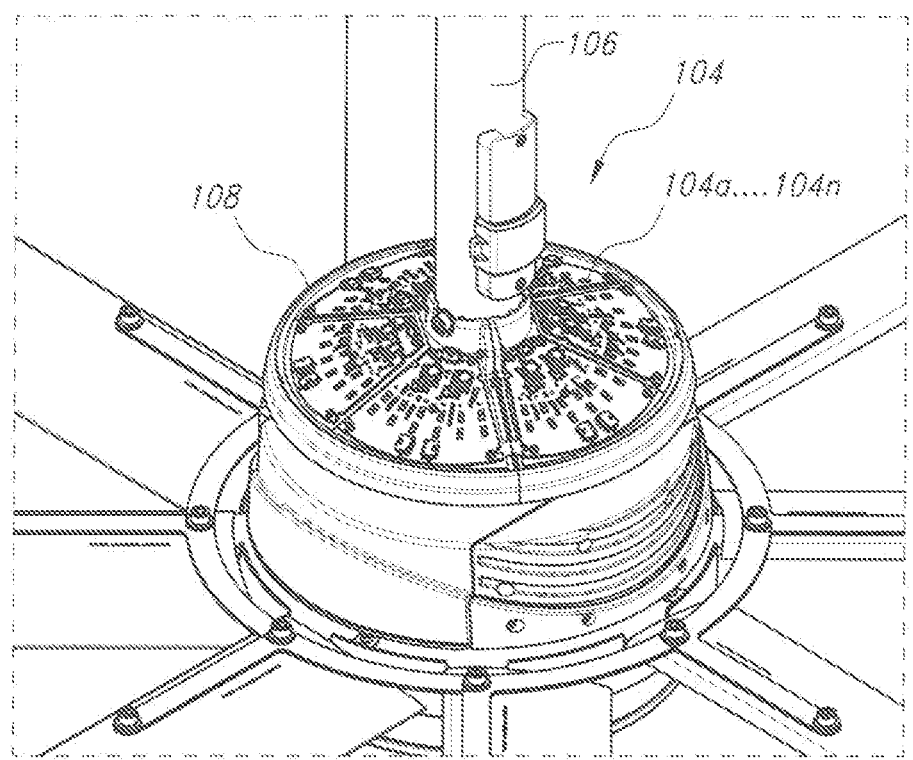
Figure 24:
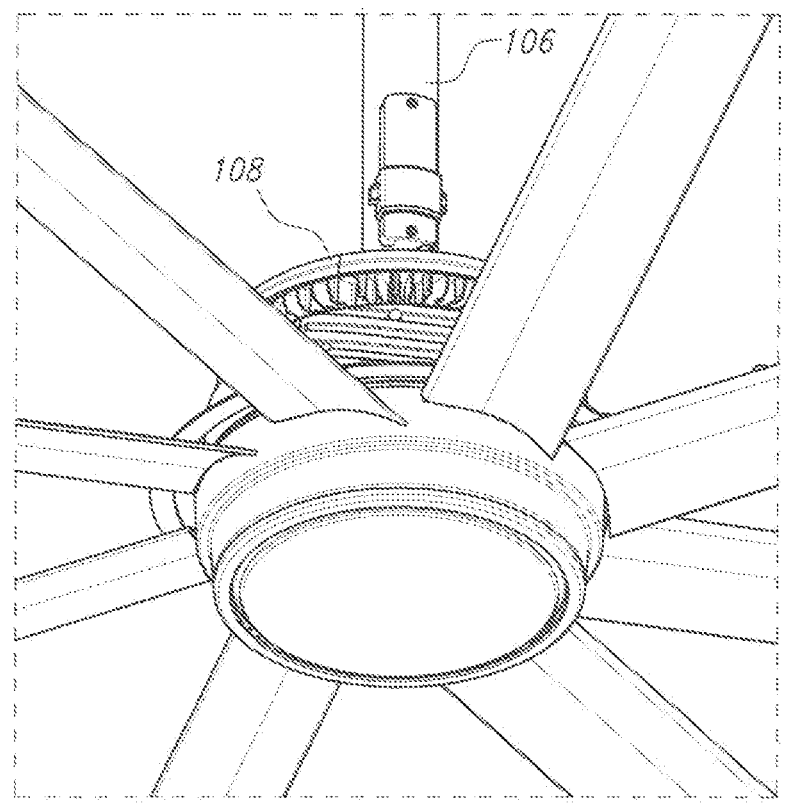

FIG. 19 illustrates that a shield 80 may be provided adjacent to (above) the module for shielding the light generated. The shield 80 may comprise a metal or other opaque structure. As indicated in FIG. 20, a portion 80a of the shield 80 may also be provided with vanes 80b or like airflow guides to help guide external air into contact with the light generated by the module 60.

FIGS. 21-26 illustrate another embodiment of a fan 100 including an uplight module 102. The module 102 includes a flexible or modular PCBA 104. The PCBA 104 may comprise a plurality of segments 104a . . . 104n that, when assembled together, form an annular structure surrounding the downtube 106 for supporting the fan 100. For example, the segments 104a . . . 104n may be semi-annular, such as in the shape of wedges.

The segments 104a . . . 104n may be interconnected by a connector, such that power is transferred to each substrate from a single power connection. Each of the segments 104a . . . 104n of the PCBA 104 may include one or more light generators, such as an LED for generating UVGI. This advantageously allows for the PCBA 104 to be placed over an existing support, such as a ceiling fan downtube 106, by removing and reconnecting one or more of the segments. As can be appreciated, this also allows for one or more of the segments 104a . . . 104n to be removed or replaced, as necessary or desired, without the need to dismount the fan 100. Wire harnesses (not shown) may be used to connect the individual boards.

Figure 25:
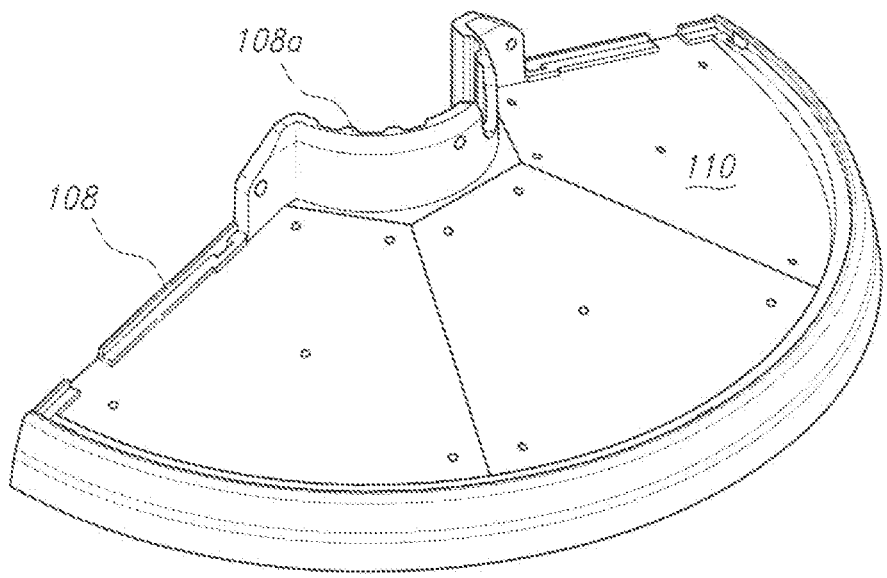
Figure 26:
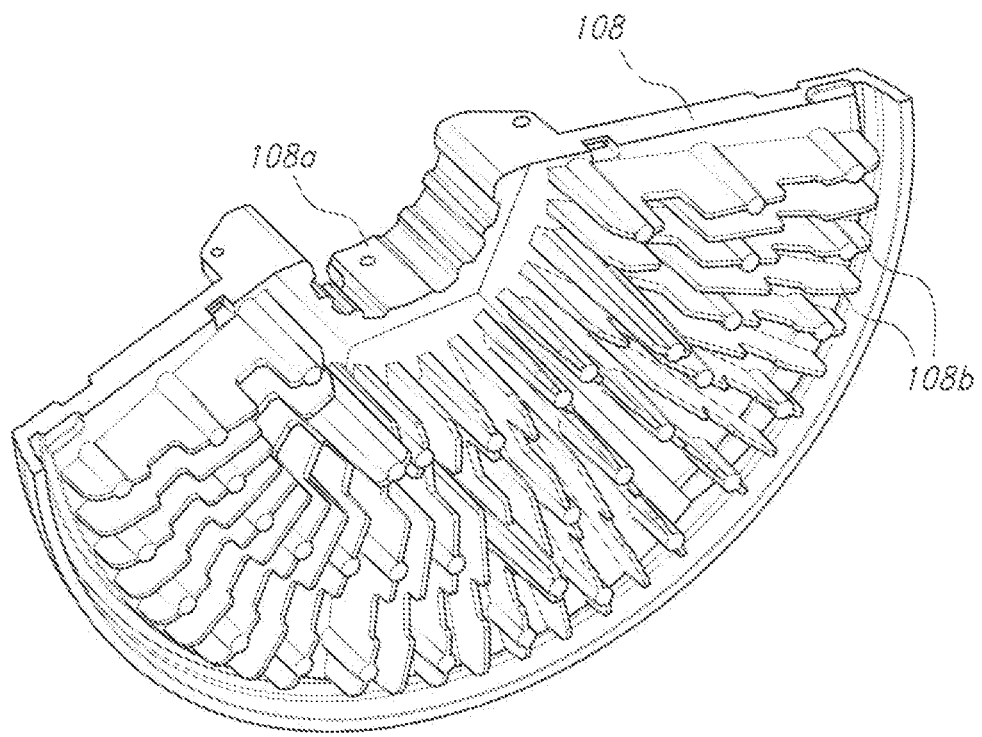

Support for the segments 104a . . . 104n may be provided by a support, which may take the form of a tray 108. As shown in FIGS. 25 and 26, the tray 108 may comprise two semi-annular halves, each with a central cutout 108a for receiving the downtube 106. The tray 108 may be provided with recessed portions 110, each for receiving one of the segments 104a . . . 104n. These portions 110 may be sloped or angled relative to a horizontal plane, such that light created by the associated segment 104a . . . 104n is directly generally upwardly and at an angle relative to a vertical axis (that is, radially outwardly relative to a central axis of the fan 100). The angle of the slope may be acute (greater than zero to less than 90 degrees) relative to a horizontal plane, and specifically may be in the range of 10-45 degrees, or more specifically, 15-20 degrees. In any case, the light generated by the associated segments 104a . . . 104n is directed outwardly into the airflow generated by the fan 100, rather than just primarily in a vertical direction, which enhances the germicidal activity by increasing the exposure of the air to the radiation being generated. The same approach to providing support to the lights at an angle may optionally be used in connection with tray 68.

The tray 108 may also contact the PCBA 104, and thus may serve to effect heat transfer therefrom. To improve conductivity, the tray 108 may comprise a conductor, such as metal, and may be a solid piece of material. As indicated in FIG. 26, the tray 108 may also include heat dissipating structures, such as spaced, radially extending fins 108b that project from the underside thereof and which may be spaced above the hub to maximize airflow thereon as a result of the operation of the associated fan blades. The segments 104a . . . 104b may lie directly on the tray 108 and be in continuous contact so as to maximize the heat transfer capabilities afforded.

FIG. 27 further illustrates that the tray 108 may be adapted to support the lights and, in particular the segments 104a ... 104b at an angle α. In the illustrated embodiment, this is achieved by providing an angled surface 108c of the tray 108, which may be recessed (and thus may correspond to recessed portion 110 noted above, but need not be recessed). As can be understood, this annular recessed portion of the tray 108 is formed by an inner wall defining an opening for receiving the support and an outer wall including or forming a peripheral lip. The annular recessed portion in this embodiment receives the circuit board in a position so that an outer edge or portion of the circuit board is below the peripheral lip or outer wall, and an inner edge or portion of the circuit board is below the inner wall. The angle α at which each segment 104a ... 104b is maintained is approximately 20 degrees relative to a horizontal plane. This maintains the LED 70a on each circuit board resting on the angled surface 108c of the tray 108 at an angle β relative to a vertical axis of approximately 18 degrees. In other words, each LED 70a is maintained at an angle relative to either a horizontal and vertical plane. In any case, the arrangement is such that the light projected by the LEDs of the tray 108 is not directed vertically, but rather at an angle to the vertical axis, and thus toward the path of airflow generated by the radially outward rotating blades of the associated fan 100 (or fan 10, if used therein).

In any version, the fan 10, 100 may also be adapted to provide an indication as to when the germicidal LEDS are approaching the end of their useful life in terms of providing effective germicidal capability. With reference to FIG. 28, a control 200, such as a wall controller, may provide a speed reference to the fan to indicate the desired fan speed to a fan motor controller 201, which may be user-defined. This speed reference signal may be monitored by a light control board 202 associated with the fan, with the assumption that if the fan is running, the light board 204 is energized and the LEDs are turned on.

When the light board 204 is energized, a time counting circuit 206 in the light control board 202 tracks the amount of time the LEDs are turned on. This is an accumulated time from when the unit was built in the factory to the present. Once the accumulated time reaches a defined threshold (such as corresponding to 5% of the remaining rated life of the LEDs), the light control board 202 may signal to a user that it is time to replace the lights. For example, the board 202 may cycle the light board 204 and consequently the LEDs on/off for a defined period of time (e.g., 5 seconds on, 5 seconds off), which indicates to the user the need for service or replacement of the LEDs. Alternatively, the signal may be provided via the control 200.

According to a further aspect of the disclosure, and with reference to FIG. 29, it may be desirable to adjust the intensity of the germicidal light due to various situational factors (e.g., room size, ceiling height, type of space, number of occupants, etc). To regulate the light, a circuit provided on the light control board 300 connected to the light board 304 may provide a means for light intensity adjustment 302. This adjustment can be in the form of a manual adjustment (i.e., screwdriver), a wired adjustment (i.e., wall control), or a wireless adjustment (i.e., remote). In one example, a set of switches on the control board 300 may be placed among different settings (four, for example), to increase or decrease the intensity of the UV light output from among pre-selected values (e.g., 250 mA, 300 mA, 350 mA, 400 mA). The light intensity is directly proportional to the drive current (e.g., a 13% reduction in drive current is a 13% reduction in light intensity). This adjustment may be done during initial installation, and may be based upon one or more factors, including the size of room, number of occupants, desired efficacy, etc.

EXAMPLE

To test the efficacy of a fan including the UV uplight, a metal and glass sealed containment room (20'W×8'H×8'D) with sealed seams was used as a directed aerosol testing chamber. A single exhaust and intake vent was covered with bleach-soaked HEPA filters at one end of the room to allow outside oxygen to enter the room. Airflow into the room was minimal and was not registered on the vane anemometer. The air temperature fluctuated slightly through the test and ranged from 74.2 F to 76.28 F. During control testing and the viral load tests, the temperature fluctuation was consistent. The ambient humidity inside the test chamber was 53.7%.

Two fans according to FIG. 1 were installed inside the containment room with a 58" extension pole to allow them to hang down. Each fan was placed at approximately the center line of the room 5' from the exterior walls and wired up to a constant power supply. During the test, the fans were turned to the fastest blade speed setting, and from two feet away, airflow was measured using a vane anemometer. Fans were run for 3 minutes prior to measuring airflow to allow them to reach proper revolutions and air speed was averaging between 330-380 FT/min. During the test, the room remained closed and sealed with staff staying inside the room until test completion. Prior to starting the tests, the fans were turned on and operational for 3 minutes to reach normal speeds. Viral media was aerosolized using a DeVilbiss™ Nebulizer at the center point of the chamber.

At specified time points, air samples were taken through the center of the room using a Biotest RCS Handheld Microbial Air sampler with an agar media strip. Sample sizes were set to 5 liters of air per sample draw. After each sample was taken, it was sealed in a plastic sterile container and only opened prior to sample storage. Each of the 8 samples collected were subject to the same TCID50 assay protocol to determine viral concentration. Each collected swab was vortexed for 1 full minute in 1 ml viral preservation media prior to serial dilution. The results are as shown in FIG. 30, illustrating that a 99.9% reduction in airborne virus was achieved in less than 20 minutes of fan operation.

Summarizing, the disclosure may relate to the following items:

1. A fan adapted to be mounted to a ceiling, comprising:
   a hub connected to a plurality of fan blades;
   a motor adapted to rotate the hub;
   a support adapted to support the hub and motor from the ceiling; and
   a tray adapted to receive the support, the tray including one or more lights for providing ultraviolet germicidal light.
2. The fan according to item 1, wherein the one or more lights, preferably LEDs, are provided on a circuit board.
3. The fan according to item 2, wherein the circuit board comprises an annular structure including a plurality of interconnected substrates, each of the plurality of substrates including at least one light emitting diode for generating ultraviolet germicidal light (e.g., UV-C).
4. The fan according to item 2 or item 3 wherein the tray is adapted to support one or more lights or the circuit board at an angle relative to a horizontal plane.
5. The fan according to any of items 2-4, further including a lens for overlying the circuit board.
6. The fan according to any of items 2-5, wherein the circuit board is flexible.

7. The fan according to any of items 2-6, wherein the circuit board is C-shaped.

8. The fan according to any of items 2-7, wherein the circuit board comprises at least two semi-annular portions connected by a connector.

9. The fan according to any of items 2-8, wherein the circuit board includes one or more lights adapted for generating non-ultraviolet light.

10. The fan according to any of items 2-9, further including a controller for controlling a wavelength of light produced by the one or more lights.

11. The fan according to any of items 2-10, further including a circuit for generating a signal indicative of a need to service the one or more lights based on a time of operation of the motor.

12. The fan according to any of items 2-11, further including a shield for shielding the one or more lights.

13. The fan according to any of items 2-12, further including a vane for guiding air toward the one or more lights.

14. The fan according to any of items 2-13, wherein the tray includes a plurality of fins for promoting heat exchange.

15. The fan according to any of items 2-14, wherein the tray includes a stanchion adapted to engage the support, and further including a fastener for fastening the stanchion to the support.

16. A fan adapted to be mounted to a ceiling, comprising:
   a hub connected to a plurality of fan blades;
   a motor adapted to rotate the hub;
   a support adapted to support the hub and motor from the ceiling; and
   a modular circuit board adapted for positioning around the support without dismounting the support from the ceiling.

17. The fan according to item 16, wherein the modular circuit board includes one or more lights adapted to provide ultraviolet germicidal light (e.g., UV-C) toward the ceiling.

18. The fan according to item 16 or item 17, further including a circuit for generating a signal indicative of a need to service the one or more lights based on a time of operation of the motor.

19. The fan according to any of items 16-18, wherein the modular circuit board comprises a plurality of semi-annular segments adapted to connect together to form an annular structure surrounding the support.

20. The fan according to any of items 16-19, wherein the tray is adapted to support the circuit board, or one or more lights for generating ultraviolet energy, at an angle relative to a horizontal plane.

21. The fan according to claim 16, wherein the circuit board includes one or more LEDs for generating UV-C radiation.

22. A fan adapted to be mounted to a ceiling, comprising:
   a hub connected to a plurality of fan blades;
   a motor adapted to rotate the hub;
   a housing for housing the motor;
   a support adapted to support the hub and motor from the ceiling; and
   an uplight module connected to the support, the uplight module including one or more LEDs directed at an angle relative to a horizontal plane.

23. The fan according to item 22, wherein the uplight module comprises a tray adapted to receive the support.

24. The fan according to item 23, wherein the tray is adapted to support one or more LEDs at an angle relative to a horizontal plane.

25. The fan according to item 24, wherein the one or more LEDs are adapted to generate ultraviolet germicidal radiation.

26. The fan according to any of items 24-25, further including a circuit for generating a signal indicative of a need to service the one or more LEDs based on a time of operation of the motor.

27. A fan adapted to be mounted to a ceiling, comprising:
   a hub connected to a plurality of fan blades;
   a motor adapted to rotate the hub;
   one or more lights for providing ultraviolet germicidal light; and
   a controller for controlling activation of the lights based on either (i) fan speed; or (ii) a motion sensor.

28. The fan according to item 27, wherein the controller controls activation of the one or more lights based on an indication that a fan speed is above a pre-determined amount.

29. The fan according to item 27, wherein the controller controls activation of the one or more lights based on an indication by the motion sensor that motion is not present.

30. The fan according to item 27, further including a circuit for generating a signal indicative of a need to service the one or more lights based on a time of operation of the motor.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Each of the following terms written in singular grammatical form: "a", "an", and "the", as used herein, means "at least one", or "one or more". Use of the phrase "one or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or the context clearly dictates otherwise. For example, the phrases: "a unit", "a device", "an assembly", "a mechanism", "a component," "an element", and "a step or procedure", as used herein, may also refer to, and encompass, a plurality of units, a plurality of devices, a plurality of assemblies, a plurality of mechanisms, a plurality of components, a plurality of elements, and a plurality of steps or procedures, respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated components), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase "consisting essentially of." Each of the phrases "consisting of" and "consists of, as used herein, means "including and limited to". The phrase "consisting essentially of" means that the stated entity or item (system, system unit, system sub-unit device, assembly, sub-assembly, mechanism, structure, component element or, peripheral equipment utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional feature or characteristic" being a system unit system sub-unit device, assembly, sub-assembly, mechanism, structure, component or element or, peripheral equipment utility, accessory, or material, step or procedure, sub-step or sub-procedure), but only if each such additional feature or characteristic" does not materially alter the basic novel and inventive characteristics or special technical features, of the claimed item.

The term "method", as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Terms of approximation, such as the terms about, substantially, approximately, generally, etc., as used herein, refer to ±10% of the stated numerical value or as close as possible to a stated condition.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment may also be illustratively described and presented in the context or format of a plurality of separate embodiments.

Having shown and described various embodiments, further adaptations of the inventive aspects described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not necessarily required. Accordingly, the scope of the present invention should be considered in terms of the claims and is understood not to be limited to the details of structure and operation shown and described in the specification and drawings.

The invention claimed is:

1. A fan adapted to be mounted to a ceiling, comprising:
   a hub connected to a plurality of fan blades;
   a motor adapted to rotate the hub;
   a housing for housing the motor;
   a support adapted to support the hub and motor from the ceiling; and
   an uplight module connected to the support, the uplight module including one or more LEDs associated with a circuit board in the form of an annular ring surrounding the support, the one or more LEDs arranged to project light toward the ceiling when the fan is mounted thereto;
   wherein the uplight module comprises an annular recessed portion formed by an inner wall defining an opening for receiving the support and a peripheral lip, the annular recessed portion receiving the circuit board in a position so that an outer edge of the circuit board is below the peripheral lip, and an inner edge of the circuit board is below the inner wall.

2. The fan according to claim 1, wherein the one or more LEDs are adapted to generate UV-C light.

3. The fan according to claim 1, further including a circuit for generating a signal indicative of a need to service the one or more LEDs.

4. The fan according to claim 1, wherein the circuit board is adapted to be positioned substantially around the support without dismounting the support from the ceiling.

5. The fan according to claim 1, wherein the annular recessed portion includes an upper support surface sloped at an acute angle relative to a horizontal plane.

6. The fan according to claim 1, wherein the circuit board comprises a plurality of semi-annular segments adapted to connect together around the support.

7. The fan according to claim 6, wherein the plurality of semi-annular segments are connected by a flexible connector.

8. The fan according to claim 1, wherein the circuit board comprises a portion that is C-shaped.

9. The fan according to claim 1, further including a translucent lens overlying the circuit board.

10. The fan according to claim 1, wherein the annular recessed portion includes an upper support surface that is sloped at an angle of 10-45 degrees relative to a horizontal plane.

11. A fan adapted to be mounted to a ceiling, comprising:
    a hub connected to a plurality of fan blades;
    a motor adapted to rotate the hub;
    a housing for housing the motor;
    a support adapted to support the hub and motor from the ceiling; and
    an uplight module connected to the support above the hub, the uplight module including one or more lights in the form of LEDs associated with a circuit board in the form of an annular ring comprising a plurality of segments surrounding the support for supporting the circuit board, wherein the one or more LEDs are supported by the support and arranged so as to project light toward the ceiling when the fan is mounted thereto;
    wherein the uplight module comprises an annular recessed portion including a recessed portion formed by an inner wall defining an opening for receiving the support, and a peripheral lip, the annular recessed portion receiving the circuit board in a position so that an outer edge of the circuit board is below the peripheral lip, and an inner edge of the circuit board is below the inner wall.

12. The fan according to claim 11, wherein the one or more LEDs are adapted to generate UV-C light.

13. The fan according to claim 11, further including a circuit for generating a signal indicative of a need to service the one or more LEDs.

14. The fan according to claim 11, wherein the circuit board is adapted to be positioned substantially around the support without dismounting the support from the ceiling.

15. The fan according to claim 14, wherein the circuit board further includes one or more LEDs adapted to provide ultraviolet germicidal light toward the ceiling.

16. The fan according to claim 14, wherein the circuit board comprises a plurality of semi-annular segments.

17. The fan according to claim 16, wherein the plurality of semi-annular segments are connected by a flexible connector.

18. The fan according to claim 14, wherein the circuit board comprises a C-shaped portion.

19. The fan according to claim 11, further including a translucent lens overlying the circuit board.

20. A fan adapted to be mounted to a ceiling, comprising:
a hub connected to a plurality of fan blades;
a motor adapted to rotate the hub;
a housing for housing the motor;
a support adapted to support the hub and motor from the ceiling; and
an uplight module connected to the support, the uplight module comprising an annular tray including a peripheral lip and one or more lights in the form of LEDs connected to an annular circuit board located within an annular recessed portion of the annular tray so as to project light from the one or more lights toward the ceiling when the fan is mounted thereto, the annular recessed portion formed by an inner wall defining an opening for receiving the support and an outer wall, the annular recessed portion receiving the annular circuit board in a position so that an outer edge of the annular circuit board is below the outer wall, and an inner edge of the circuit board is below the inner wall.

21. The fan according to claim 20, wherein the annular circuit board comprises a plurality of interconnected segments around the opening for receiving the support.

22. The fan according to claim 20, further including a circuit for generating a signal indicative of a need to service the one or more lights.

23. The fan according to claim 20, wherein the annular circuit board is adapted to be positioned substantially around the support without dismounting the support from the ceiling.

24. The fan according to claim 23, wherein the annular circuit board includes a C-shaped portion.

25. The fan according to claim 23, wherein the annular circuit board comprises a plurality of semi-annular segments adapted to connect together to form an annular structure surrounding the support.

26. The fan according to claim 25, wherein the plurality of semi-annular segments are connected by a flexible connector.

27. A fan adapted to be mounted to a ceiling, comprising:
a hub connected to a plurality of fan blades;
a motor adapted to rotate the hub;
a housing for housing the motor;
a support adapted to support the hub and motor from the ceiling; and
an uplight module connected to the support above the hub, the uplight module including one or more lights in the form of LEDs for generating ultraviolet germicidal radiation, the uplight module including an annular tray having a peripheral lip and a central opening for receiving the support, a fastener for fastening the annular tray to the support, and an annular recessed portion adapted to support the one or more lights so at to project the ultraviolet germicidal radiation toward the ceiling when the fan is mounted thereto, the annular recessed portion formed by an inner wall defining the central opening for receiving the support and an outer wall, the annular recessed portion receiving a circuit board in a position so that an outer portion of the circuit board is below the outer wall, and an inner portion of the circuit board is below the inner wall.

* * * * *